(12) United States Patent
Axelson, Jr. et al.

(10) Patent No.: US 12,083,021 B2
(45) Date of Patent: *Sep. 10, 2024

(54) GLENOID IMPLANT

(71) Applicant: Encore Medical, L.P., Austin, TX (US)

(72) Inventors: Stuart L. Axelson, Jr., Succasunna, NJ (US); Catherine Ann Hamann, Chester, NY (US); Katherine Victoria Ackley, Falls Church, VA (US); Grant Lieder Tribble, Hagerstown, MD (US); Shreyas Sriram, Sammamish, WA (US)

(73) Assignee: ENCORE MEDICAL, L.P., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,381

(22) Filed: Jan. 25, 2023

(65) Prior Publication Data

US 2023/0165686 A1 Jun. 1, 2023

Related U.S. Application Data

(63) Continuation of application No. 17/594,573, filed as application No. PCT/US2020/029947 on Apr. 24, 2020, now Pat. No. 11,589,998.

(Continued)

(51) Int. Cl.
*A61F 2/40* (2006.01)
*A61F 2/30* (2006.01)
*A61F 2/46* (2006.01)

(52) U.S. Cl.
CPC ........ *A61F 2/4081* (2013.01); *A61F 2/30749* (2013.01); *A61F 2002/30327* (2013.01);

(Continued)

(58) Field of Classification Search
None
See application file for complete search history.

(56) References Cited

U.S. PATENT DOCUMENTS 5,702,447 A * 12/1997 Walch .................. A61F 2/4081
606/327
5,702,477 A 12/1997 Walch et al.
(Continued)

FOREIGN PATENT DOCUMENTS

DE 10123517 C1 * 11/2002 ........... A61F 2/4014

OTHER PUBLICATIONS

International Search Report and Written Opinion of International Searching Authority for Application No. PCT/US2020/029947, mailed Jul. 29, 2020 (8 pages).

*Primary Examiner* — Ann Schillinger
(74) *Attorney, Agent, or Firm* — Nixon Peabody LLP

(57) ABSTRACT

A glenoid implant includes a body, a plurality of fins, a collet, and a plug. The body has a central aperture therethrough and a plurality of slots. Each of the plurality of fins are coupled with a respective one of the plurality of slots of the boss of the body such that each of the plurality of fins is configured to move from a first generally inward position towards a second generally outward position. The collet including an interior threaded bore and a plurality of deflectable arms. The plug includes a threaded portion and a tip portion configured to engage with and cause the plurality of deflectable arms of the collet to move and cause the plurality of fins to move from the first generally inward position towards the second generally outward position, thereby aiding in securing the body to a scapula of a patient.

7 Claims, 25 Drawing Sheets

Related U.S. Application Data

(60) Provisional application No. 62/838,633, filed on Apr. 25, 2019.

(52) U.S. Cl.
CPC ............ *A61F 2002/30405* (2013.01); *A61F 2002/30579* (2013.01); *A61F 2002/30901* (2013.01); *A61F 2002/4085* (2013.01)

(56) References Cited

U.S. PATENT DOCUMENTS

| | | | |
|---|---|---|---|
| 11,589,998 B2* | 2/2023 | Axelson, Jr. | A61F 2/4081 |
| 2004/0220674 A1* | 11/2004 | Pria | A61F 2/40 |
| | | | 623/19.12 |
| 2007/0055380 A1* | 3/2007 | Berelsman | A61F 2/4612 |
| | | | 623/908 |
| 2007/0150065 A1* | 6/2007 | Angibaud | A61F 2/389 |
| | | | 623/20.14 |
| 2007/0219637 A1 | 9/2007 | Berelsman et al. | |
| 2010/0274359 A1* | 10/2010 | Brunnarius | A61F 2/30734 |
| | | | 623/19.13 |
| 2012/0209392 A1* | 8/2012 | Angibaud | A61F 2/4081 |
| | | | 623/19.11 |
| 2013/0123930 A1* | 5/2013 | Burt | A61F 2/4003 |
| | | | 623/19.14 |
| 2013/0150972 A1* | 6/2013 | Iannotti | A61F 2/4059 |
| | | | 623/18.11 |
| 2013/0261752 A1 | 10/2013 | Lappin et al. | |
| 2014/0194995 A1* | 7/2014 | Koka | A61F 2/4637 |
| | | | 623/19.11 |
| 2015/0305877 A1 | 10/2015 | Gargac et al. | |
| 2017/0367836 A1* | 12/2017 | Cardon | A61B 17/8605 |
| 2018/0161169 A1* | 6/2018 | Cardon | A61F 2/4081 |
| 2021/0401584 A1* | 12/2021 | Gargac | A61F 2/4014 |

* cited by examiner

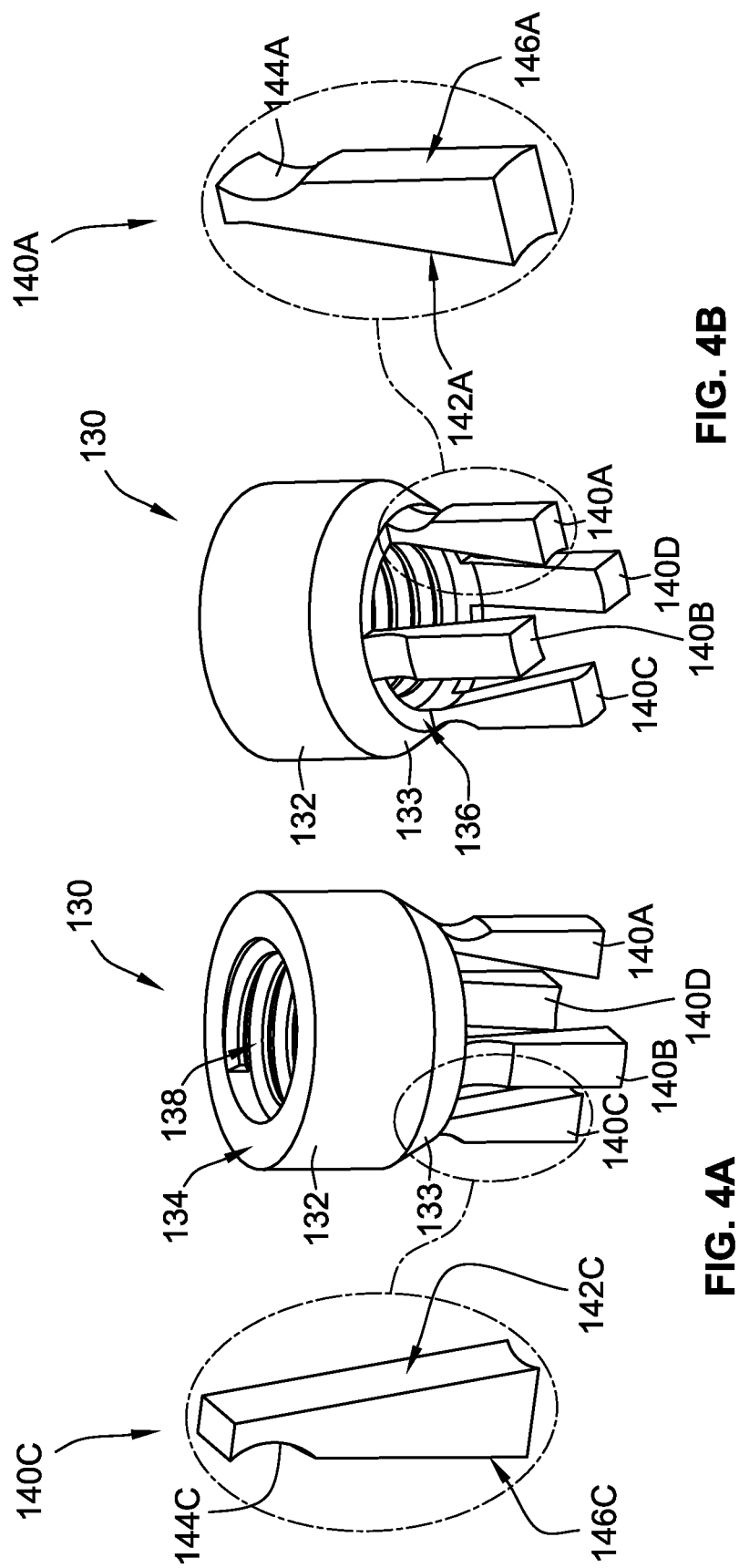

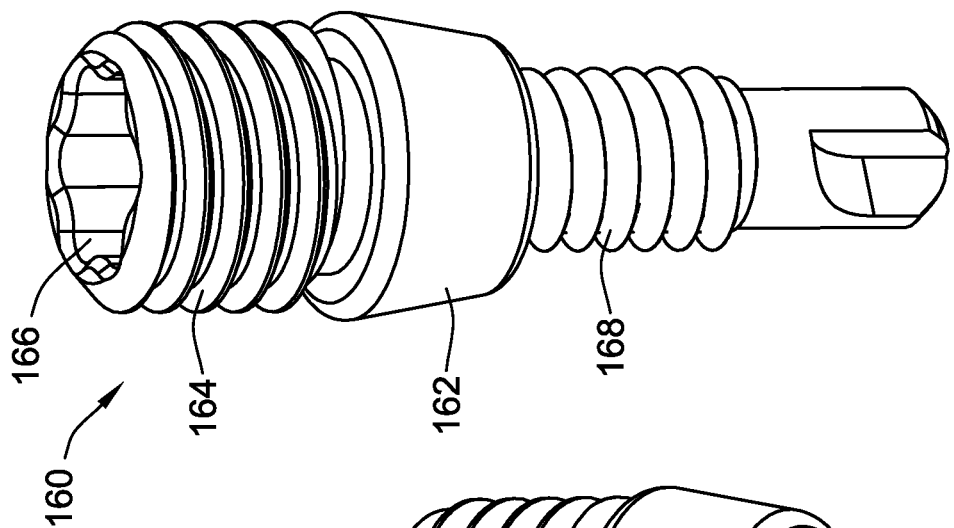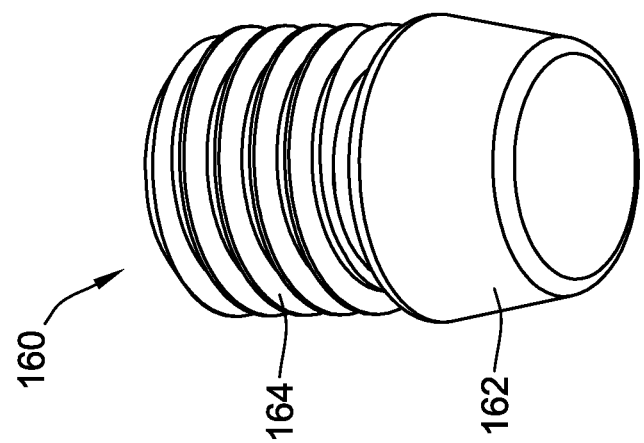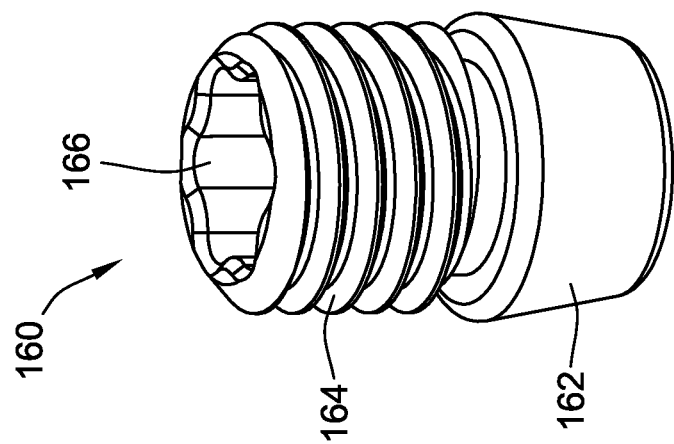

GLENOID IMPLANT

CROSS-REFERENCE TO RELATED APPLICATION

This application is a continuation of U.S. application Ser. No. 17/594,573, filed Nov. 10, 2022, which is the U.S. national phase of International Application No. PCT/US2020/029947, filed Apr. 24, 2020, which claims the benefit of U.S. Provisional Application No. 62/838,633, filed Apr. 25, 2019, the disclosure of each of which is hereby incorporated by reference herein in its entirety.

TECHNICAL FIELD

The present disclosure relates generally to glenoid implants.

BACKGROUND

Shoulder replacement surgery (arthroplasty) is often used to treat patients suffering from pain due to worn or damaged shoulder joints (e.g., caused by arthritis and/or injury). The shoulder comprises three bones: the humerus (upper arm bone), scapula (shoulder blade), and clavicle (collarbone). A ball or head at one end of the humerus fits into a glenoid to allow rotation. In shoulder replacement surgery, damaged parts are removed and replaced with a prosthesis. Because tens of thousands of shoulder arthroplasty surgeries are performed each year in the United States, there remains a need for improved glenoid implants. The present disclosure is directed to solving these and other problems and needs.

SUMMARY

According to some implementations of the present disclosure, a glenoid implant includes a body, a plurality of fins, a collet, and a plug. The body has a central aperture therethrough and includes a boss coupled to and extending from a plate. The boss includes a plurality of slots. Each of the plurality of fins are coupled with a respective one of the plurality of slots of the boss of the body such that each of the plurality of fins is configured to move from a first generally inward position towards a second generally outward position. The collet includes an interior threaded bore and a plurality of deflectable arms. The collet is configured to be at least partially received within the central aperture of the body such that each of the plurality of deflectable arms is generally adjacent to a respective one of the plurality of slots of the boss of the body. The plug includes an exterior threaded portion and a tip portion. The exterior threaded portion of the plug is configured to threadingly engage with the interior threaded bore of the collet such that the tip portion of the plug is configured to engage with and cause the plurality of deflectable arms of the collet to move and cause the plurality of fins to move from the first generally inward position towards the second generally outward position, thereby aiding in securing the body to a scapula of a patient.

According to some implementations of the present disclosure, a glenoid implant includes a body, a collet, a plug, and a plurality of fins. The body has a central aperture therethrough. The collet is configured to be received within the central aperture of the body, the collet having an interior threaded bore and a plurality of deflectable arms. The plug includes a threaded portion configured to threadingly engage the interior threaded bore of the collet, the plug being configured to be engaged by a tool to rotate the plug such that the plug moves in a first axial direction to cause the plurality of deflectable arms to deflect radially outward relative to a central axis of the central aperture. The plurality of fins are configured to move radially outward from a first position towards a second generally outward position responsive to deflection of the plurality of deflectable arms to aid in securing the body to a scapula of a patient.

According to some implementations of the present disclosure, a method of installing a glenoid implant in bone of a patient includes positioning a body, a collet, and a plurality of fins in a cavity formed in the bone, the collet including an interior threaded bore. The method also includes threading a plug into the interior threaded bore of the collet by rotating the plug in a first rotational direction, thereby causing the plug to move in a first axial direction. The method further includes continuing to thread the plug into the interior threaded bore of the collet such that a tapered tip of the plug engages the plurality of fins, thereby causing the plurality of fins to move radially outward from a first generally inward position towards a second generally outward position to aid in securing the glenoid implant to the bone of the patient.

According to some implementations of the present disclosure, a glenoid implant includes a body and a plug. The body has a boss coupled to and extending from a plate and an interior threaded bore. The boss includes a plurality deflectable portions configured to move from a first position towards a second position. The plug includes a tip portion and an exterior threaded portion The exterior threaded portion of the plug is configured to threadingly engage the interior threaded bore of the body such that rotation of the plug causes the plug to move in a first axial direction relative to the body and such that the tip portion engages the plurality of deflectable portions of the boss, thereby causing the plurality of expandable portions to move from a first position towards a second position to aid in securing the glenoid implant to bone of a patient.

The above summary is not intended to represent each implementation or every aspect of the present disclosure. Additional features and benefits of the present disclosure are apparent from the detailed description and figures set forth below.

BRIEF DESCRIPTION OF THE DRAWINGS

FIG. 4A is a first perspective view of a collet of the glenoid implant, according to some implementations of the present disclosure;

FIG. 4B is a second perspective view of the collet of the glenoid implant, according to some implementations of the present disclosure;

FIG. 7A is a first perspective view of a plug of the glenoid implant of FIGS. 1A-2, according to some implementations of the present disclosure;

FIG. 7B is a second perspective view of the plug of the glenoid implant, according to some implementations of the present disclosure;

FIG. 7C is a perspective view of an alternative plug of the glenoid implant, according to some implementations of the present disclosure;

Figure 1A:
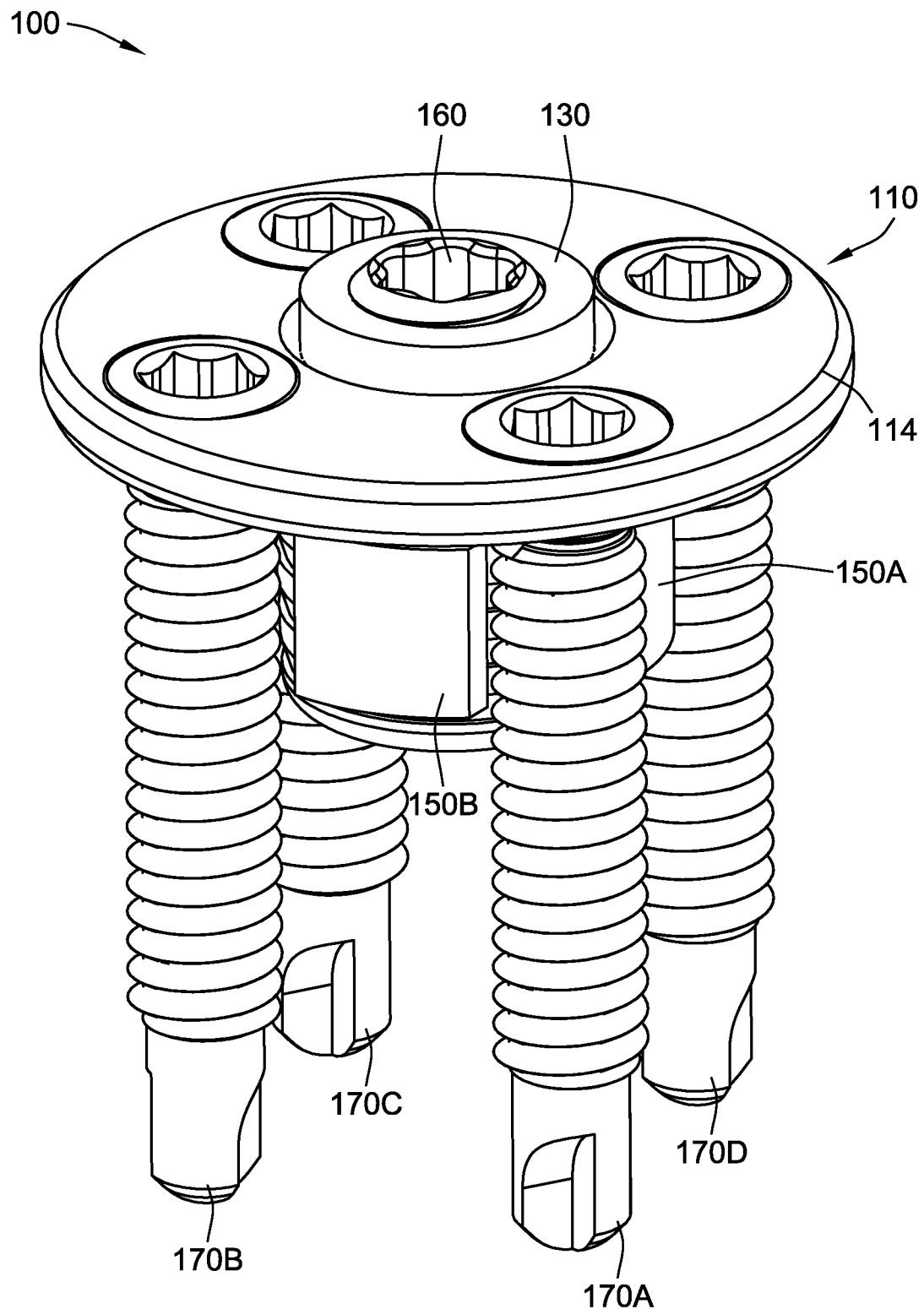
FIG. 1A is a first perspective assembled view a glenoid implant, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many glenoid (shoulder socket) implants are made completely from polyethylene and affixed to the cortical bone using bone cement (e.g., polymethylmethacrylate) and/or screws. Some glenoid implants have a metal baseplate with a polyethylene insert and are made to sit on the surface of a reamed glenoid, which is prepared by removing any remaining cartilage and flattening the bony surface. These implants use either a keel or multiple elongated pegs on the back of the prosthetic glenoid implant to secure the glenoid implant inside the glenoid vault.

Keeled and pegged glenoid implants suffer from several disadvantages, which limit their lifespan once implanted and reduce the number of indications for which they can be used when the age of the patient is a factor. For example, the glenoid implants can loosen due to poor fixation within the bone, and they are prone to wear and fatigue failure of the polyethylene due to adhesion, abrasion, and shear stress. Thus, there remains a need for improved glenoid implants that are securely implanted in the scapula of the patient.

Figure 1B:
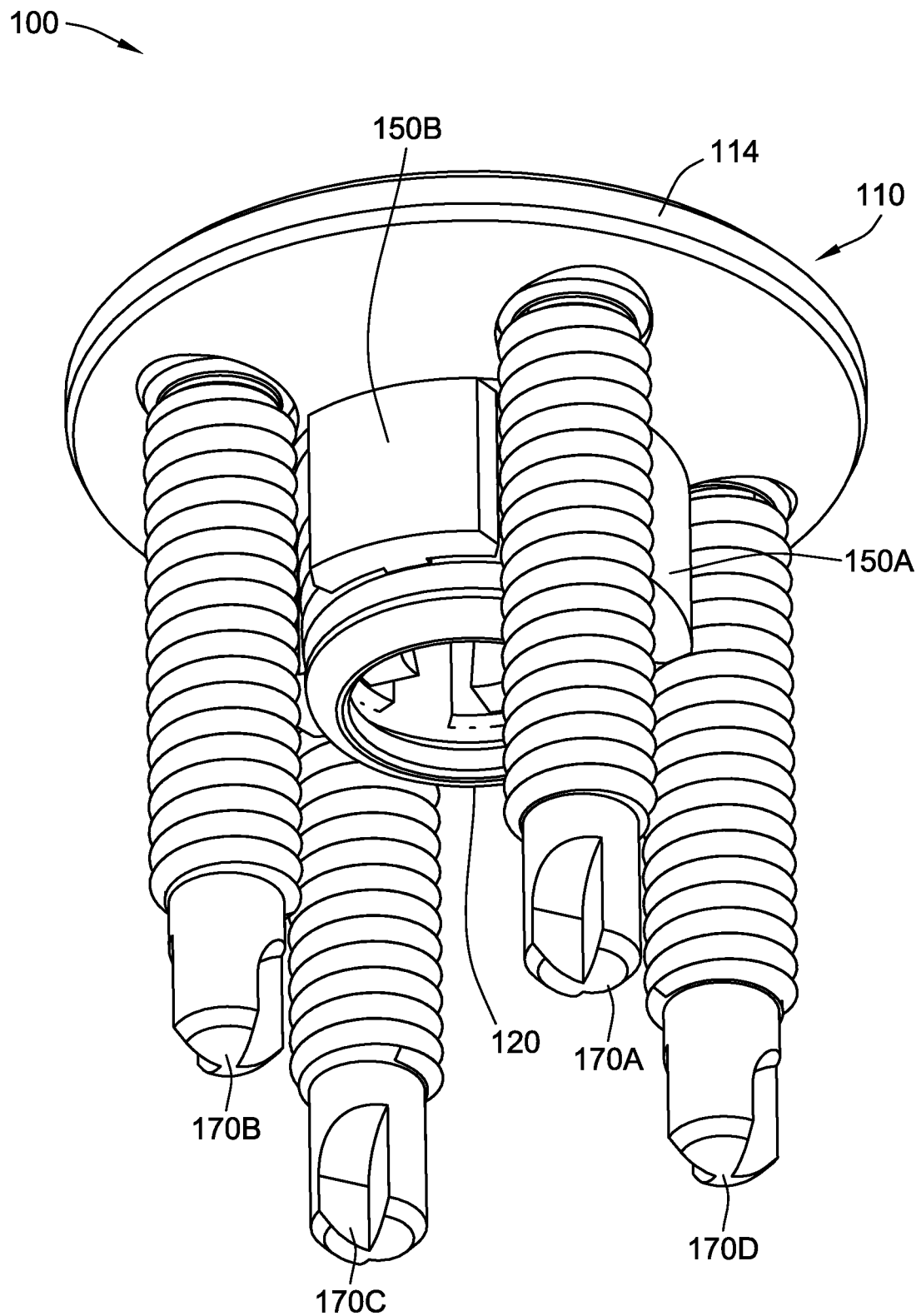
FIG. 1B is a second perspective assembled view the glenoid implant of FIG. 1A, according to some implementations of the present disclosure.
Figure 2:
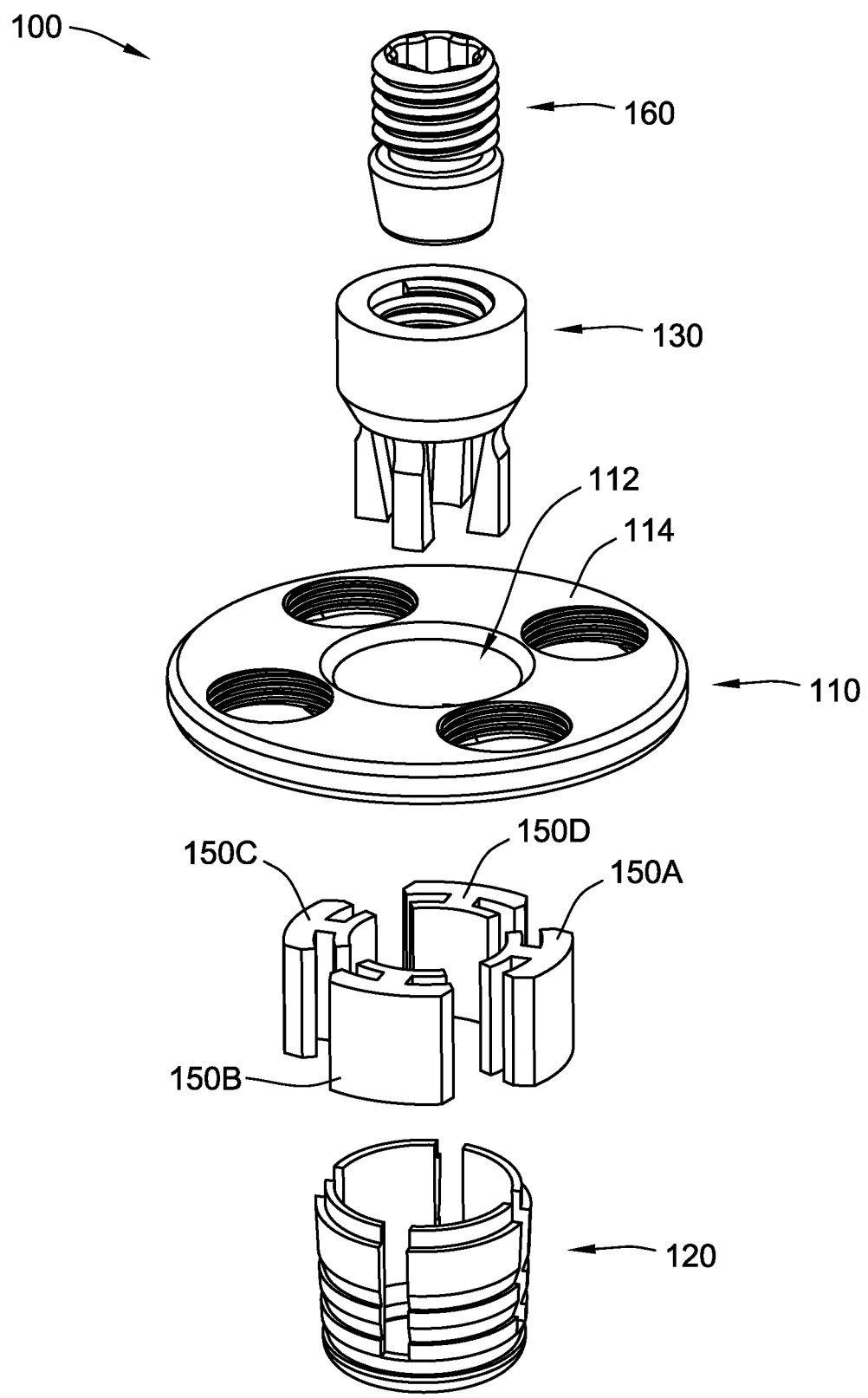
FIG. 2 is an exploded view of the glenoid implant of FIG. 1A, according to some implementation of the present disclosure.

Referring generally to FIGS. 1A-2, a glenoid implant 100 is illustrated. FIGS. 1A and 1B are assembled views of the glenoid implant 100. FIG. 2 is an exploded view of the glenoid implant 100. Generally, at least a portion of the glenoid implant 100 is received in and secured to a portion of a scapula of a patient (e.g., a glenoid cavity of the scapula).

The glenoid implant 100 includes a body 110, a collet 130, a plurality of fins 150A-150D, a plug 160, and a plurality of fasteners 170A-170D. At least a portion of the collet 130 is received within at least a portion of the body 110. Similarly, at least a portion of the plug 160 is received within at least a portion of the collet 130. As described in further detail herein, the plurality of fins 150A-150D are moveable from a first generally inward position towards a second generally outward position relative to the body 110 to engage a portion of the scapula of a patient to aid in securing the glenoid implant 100 to the scapula and/or to promote osseointegration of the glenoid implant 100.

Figure 3A:
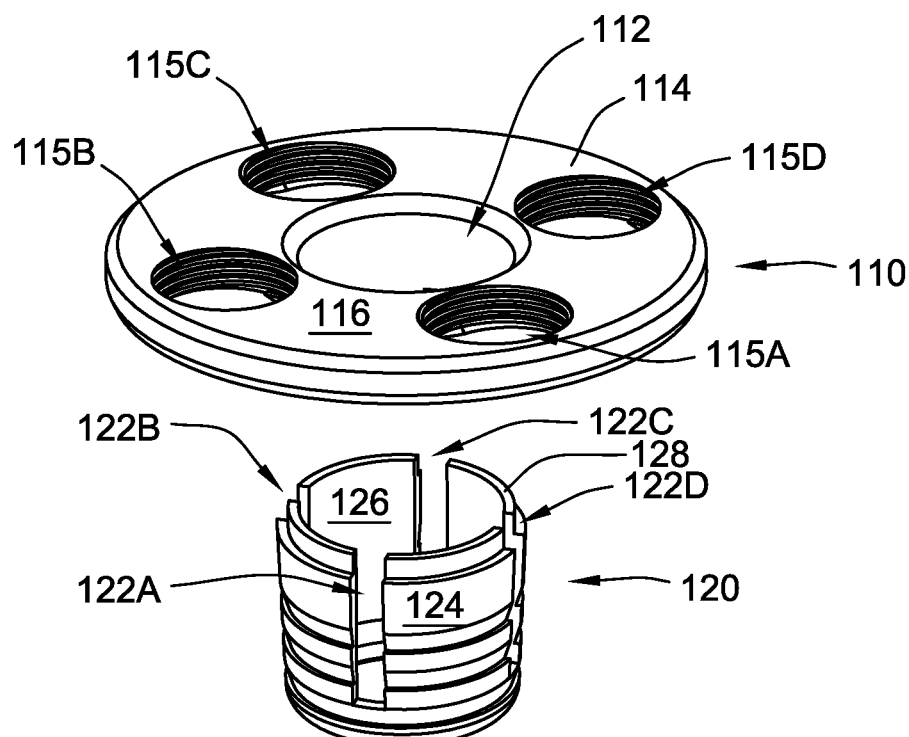
FIG. 3A is a first perspective view of a body of the glenoid implant, according to some implementations of the present disclosure.
Figure 3B:
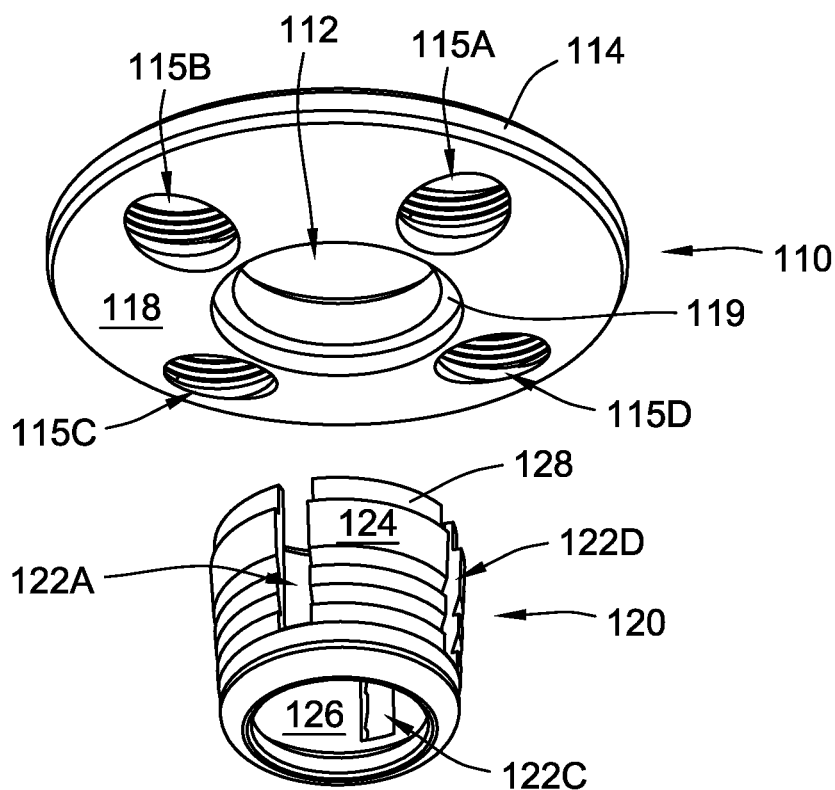
FIG. 3B is a second perspective view of the body of the glenoid implant of FIGS. 1A-2, according to some implementations of the present disclosure.

Referring to FIGS. 3A and 3B, the body 110 includes a central aperture 112 therethrough, a plate 114, and a boss 120. The body 110 and the boss 120 both comprise a metal material (e.g., stainless steel, titanium, tantalum, or alloys thereof). The central aperture 112 extends through both the plate 114 and the boss 120 of the body 110. As described in further detail herein, at least a portion of the collet 130 is received within at least a portion of the central aperture 112 when the glenoid implant 100 is in an assembled configuration. In some implementations, the central aperture 112 includes a countersink or a counterbore extending from the upper surface 116 (FIG. 3A) of the plate 114 towards the lower surface 118 (FIG. 3B) of the plate 114.

The plate 114 has a generally cylindrical or disk shape and includes an upper surface 116 (FIG. 3A) and a lower surface 118 (FIG. 3B). The plate 114 also includes a plurality of apertures 115A-115D extending from the upper surface 116 (FIG. 3A) to the lower surface 118 (FIG. 3B). As shown, the plurality of apertures 115A-115D are concentrically arranged around the central aperture 112 of the body 110. Each of the plurality of apertures 115A-115D are optionally threaded and are generally sized and shaped to receive therein at least a portion of the fasteners 170A-170D (FIGS. 1A-2) to aid in securing the glenoid implant 100 to the scapula of a patient.

The boss 120 has a generally cylindrical shape and includes a plurality of slots 122A-122D. Each of the plurality of slots 122A-122D has a generally rectangular shape. The plurality of slots 122A-122D are circumferentially arranged about the boss 120 and extend in an axial direction between an outer surface of the boss 120 and an inner surface of the boss 120. As described in further detail herein, each of the slots 122A-122D are coupled with a respective one of the plurality of fins 150A-150D (FIGS. 1A-2) such that the fins 150A-150D are moveable between a first generally inward position towards to a second generally outward position relative to the boss 120.

The boss 120 includes a shoulder 128 extending about the circumference thereof. The plate 114 also includes an opposing shoulder 119 (FIG. 3B). The shoulder 128 of the boss 120 engages the opposing shoulder 119 of the plate 114 to create a press fit connection between the plate 114 and the boss 120. The plurality of fins 150A-150D are inserted into corresponding ones of the plurality of slots 122A-122D in the boss 120 prior to forming the press fit connection between the boss 120 and the plate 114. Thus, in an assembled configuration, the boss 120 of the body 110 generally extends from the lower surface 118 (FIG. 3B) of the plate 114.

In some implementations, in addition to the press fit connection between the plate 114 and the boss 120 of the body 110, at least a portion of the boss 120 is welded to at least a portion of the plate 114 to further aid in securing the boss 120 to the plate 114. For example, a weld seam can be formed generally adjacent to the press fit connection between the shoulder 128 of the boss 120 and the opposing shoulder 119 of the plate 114 to aid in securing the plate 114 to the boss 120. The weld seam can be continuous or include a plurality of weld seams, where each of the plurality of weld seams generally extends between a pair of the plurality of apertures 115A-115D of the plate 114 (FIG. 3A).

While the plate 114 and the boss 120 are shown in FIGS. 3A-3B as being separate and distinct components that are coupled together when the glenoid implant 100 is in an assembled configuration, in some implementations, the plate 114 and the boss 120 of the body 110 are unitary and/or monolithic. As described in further detail herein, in such implementations, the plurality of fins 150A-150D can comprise two or more separate components so that the plurality of fins 150A-150D can be installed into corresponding ones of the plurality of slots 122A-122D of the boss 120.

The boss 120 of the body 110 is at least partially received in a portion of a scapula of a patient (e.g., a glenoid cavity), and the lower surface 118 of the plate 114 (FIG. 3B) engages or contacts a surface of the scapula of the patient to aid in securing the glenoid implant 100 to the scapula. To facilitate this arrangement, the plate 114 has a diameter that is greater than a diameter of the boss 120 (e.g., at least two times greater, at least three times greater, at least four times greater, etc.) to aid in securing the glenoid implant 100 to the scapula of a patient and prevent the entire glenoid implant 100 from falling into the cavity in the scapula of the patient.

Referring to FIGS. 4A and 4B, the collet 130 includes a cylindrical portion 132, an interior threaded bore 138, and a plurality of deflectable arms 140A-140D. The cylindrical portion 132 includes an upper surface 134 (FIG. 4A) and a lower surface 136 (FIG. 4B). The interior threaded bore 138 extends from the upper surface 134 (FIG. 4A) and the lower surface 136 (FIG. 4B) of the cylindrical portion 132. As discussed in further detail herein, the interior threaded bore 138 receives at least a portion of the plug 160 (FIGS. 1A-2) therein and threadingly engages the plug 160. The cylindrical portion 132 includes an inwardly tapered portion 133 that aids in securing the collet 130 within the central aperture 112 (FIG. 3A-3B) of the body 110 when the glenoid implant 100 is in an assembled configuration (e.g., via a press fit connection, a Morse press fit connection, a friction fit connection, or any combination thereof). In some implementations, the entire cylindrical portion 132 is inwardly tapered from the upper surface 134 (FIG. 4A) towards the lower surface 136 (FIG. 4B) to aid in securing the collet 130 within the central aperture 112 (FIGS. 3A and 3B) of the body 110.

The plurality of deflectable arms 140A-140D extend from the lower surface 136 (FIG. 4B) of the cylindrical portion 132. Each of the plurality of deflectable arms 140A-140D includes an inwardly tapered inner surface and an opposing outer surface. For example, the first deflectable arm 140A includes an inwardly tapered inner surface 142A, an outer curved portion 144A, and an outer flat portion 146A and the third deflectable arm 144C includes an inwardly tapered inner surface 142C, an outer curved portion 144C, and an outer flat portion 146C. The outer curved portion 144A aids in permitting the deflectable arm 140A to move or deflect radially outward relative to a central axis running through the interior threaded bore 138 of the cylindrical portion 132. As described in further detail herein, movement of deflection of the deflectable arms 140A causes at least a portion of the outer flat portion 146A to contact at least a portion of a corresponding one of the plurality of fins 150A-150D to cause the fin to move from a first generally inwardly position towards a second generally outward position.

Figure 5B:
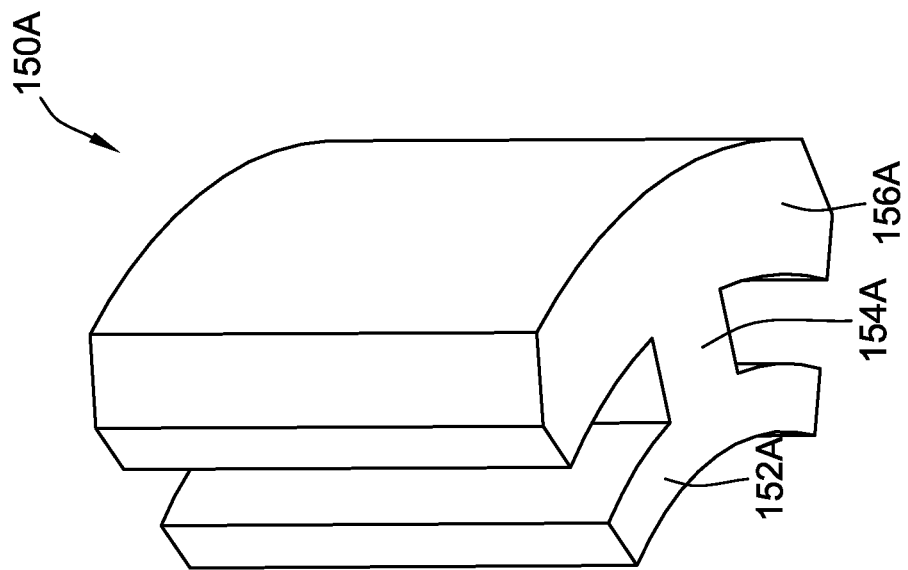
FIG. 5B is a second perspective view of the one of the plurality of fins of the glenoid implant, according to some implementations of the present disclosure.
Figure 5A:
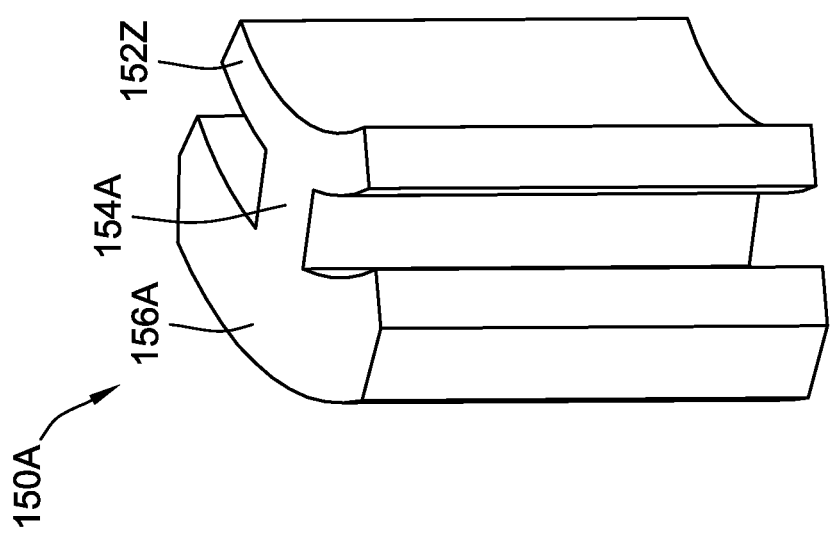
FIG. 5A is a first perspective view of one of a plurality of fins of the glenoid implant of FIG. 1A, according to some implementations of the present disclosure.

Each of the plurality of fins 150A-150D (FIGS. 1A-2) includes an interior portion, a middle portion, and an exterior portion. Referring to FIGS. 5A and 5B, a first fin 150A of the plurality of fins 150A-150D (FIGS. 1A-2) includes an interior portion 152A, a middle portion 154A, and an exterior portion 156A. The interior portion, the middle portion, and the exterior portion of each of the fins 150B-150D (FIGS. 1A-2) are the same as, or similar to, the interior portion 152A, the middle portion 154A, and the exterior portion 156A of the first fin 150A (FIGS. 5A and 5B).

In an assembled configuration of the glenoid implant 100 (FIGS. 1A-1B), the interior portion 152A of the first fin 150A is positioned between a corresponding one of the plurality of deflectable arms 140A-140D of the collet 130 (FIGS. 4A-4B) and an inner surface of the boss 120 of the body 110 (FIGS. 3A-3B). The interior portion 152A has a generally curved shape corresponding to a curvature of the inner surface of the boss 120 such that a surface of the interior portion 152A can be generally flush with the inner surface of the boss 120 (e.g., when the first fin 150A is in the second generally outward position described herein). In the assembled configuration, the middle portion 154A of the first fin 150A is positioned within a corresponding one of the plurality of slots 122A-122D (FIGS. 3A-3B) of the boss 120 of the body 110, while the exterior portion 156A of the fin 150A protrudes from an outer surface of the boss 120 of the body 110.

The exterior portion 156A has a generally curved shape corresponding to a curvature of the outer surface of the boss 120 such that a surface of the exterior portion 156A can be generally flush with the outer surface of the boss 120 (e.g., when the first fin 150A is in the first generally inwardly position described herein). The length of the middle portion 154A extending between the interior portion 152A and the exterior portion 156A permits movement of the first fin 150A relative to corresponding one of the slots 122A-122D of the boss 120 (FIGS. 3A-3B) responsive to movement of the plurality of deflectable arms 140A-140D (FIGS. 4A-4B) of the collet 130.

To position the plurality of fins 150A-150D such that they are coupled with the slots 122A-122D of the boss 120 when the glenoid implant 100 is in an assembled configuration (FIGS. 1A-1B), each of the plurality of fins 150A-150D slide into respective ones of the slots 122A-122D prior to the boss 120 being coupled to the plate 114 (e.g., via a press fit connection and/or welding) to form the body 110.

However, as described above, in some implementations, the plate 114 and the boss 120 of the body 110 (FIGS. 3A-3B) are unitary and/or monolithic rather than being separate and distinct components that are press fit and/or welded together. In such implementations, the plurality of fins 150A-150D cannot be installed into the slots 122A-122D because neither the interior portion nor the exterior portion of each of the fins 150A-150D can fit between the slots 122A-122D.

Thus, in such implementations where the body 110 is unitary and/or monolithic, (i) the exterior portion of each fin can be separate and distinct from the middle portion and the interior portion (which are unitary and/or monolithic), (ii) the interior portion of each fin can be separate and distinct from the middle portion and exterior portion (which are unitary and/or monolithic) to permit installation of the fins, or (iii) the interior portion, the middle portion, and the exterior portion are all separate distinct. In such implementations, the interior portion, the middle portion, the exterior portion, or any combination thereof can be coupled together, for example, via a welded connection (e.g., one or more tack welds), a press fit connection, a pinned connection, an adhesive connection, or any combination thereof. For example, if the interior portion and the middle portion are unitary and/or monolithic, the interior portion can be positioned within the boss 120 with the middle portion protruding through one of the slots 122A-122D. Then, the outer portion can be coupled to the middle portion (e.g., via one or more tack or spot welds) to assemble the fin.

Figure 6B:
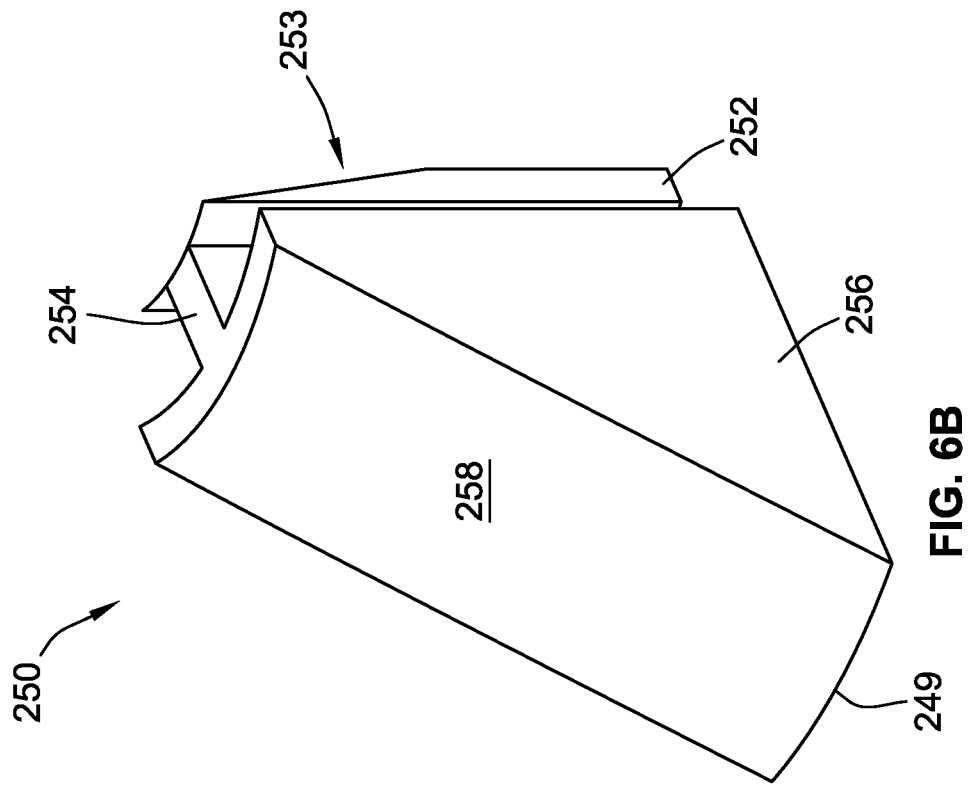
FIG. 6B is a second perspective view of the alternative fin, according to some implementations of the present disclosure.
Figure 6A:
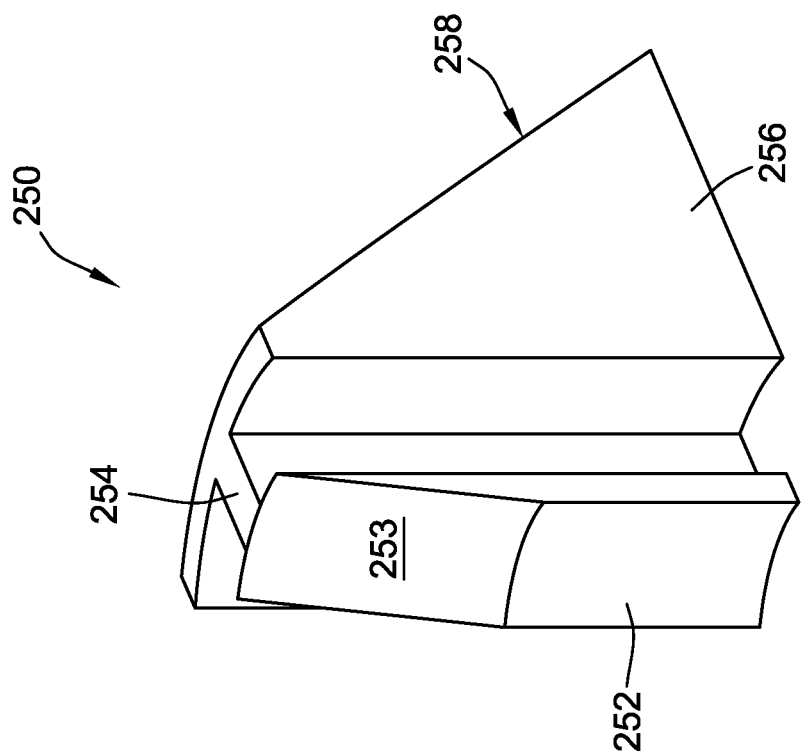
FIG. 6A is a first perspective view of an alternative fin, according to some implementations of the present disclosure.

While each of the fins 150A-150D (FIGS. 1A-2 and FIGS. 5A-5B) has been described herein as including a generally flat outer surface on the exterior portion, more generally, each of the fins 150A-150D can have any suitable shape. For example, referring to FIGS. 6A and 6B, an alternative fin 250 according to some implementations of the present disclosure is illustrated. The alternative fin 250 includes an interior portion 252, a middle portion 254, and an exterior portion 256 the same as, or similar to, the interior portion 152A, the middle portion 154, and the exterior portion 156A of the first fin 150A (FIGS. 5A-5B) described above.

The interior portion 252 of the alternative fin 250 differs from the interior portion 152A in that the interior portion 252 has an inwardly tapered surface 243. The inwardly tapered surface 343 engages a corresponding one of the plurality of deflectable arms 140A-140D of the collet 130 (FIGS. 4A-4B). The exterior portion 256 of the alternative fin 250 differs from the exterior portion 156A of the first fin 150A (FIGS. 5A-5B) in that the exterior portion 256 is generally wedge shaped and includes a tapered surface 248 and a forward edge 249. The forward edge 249 and at least a portion of the tapered surface 248 of the exterior portion 246 engage at least a portion of the scapula of the patient (e.g., spongy bone in the glenoid cavity) when the alternative fin 250 is moved to a generally outward position relative to the body 110 to aid in securing the glenoid implant 100 to the scapula and/or to promote osteointegration.

Referring to FIGS. 7A and 7B, the plug 160 includes a tip portion 162, an exterior threaded portion 164, and a socket 166. The tip portion 162 includes a generally inwardly tapered surface that engages the plurality of deflectable arms 140A-140D of the collet 130 (FIGS. 4A-4B) responsive to axial movement of the plug 160 relative to the collet 130, as described in further detail herein.

The exterior threaded portion 164 of the plug 160 at least partially threadingly engages the interior threaded bore 138 of the collet 130 when the glenoid implant 100 is in an assembled configuration (FIGS. 1A and 1B). The socket 166 receives a portion of a tool (e.g., a screwdriver, a torx key, a hex key, an Allen wrench, etc.) to permit rotation to the tool to cause rotation of the plug 160 in a first rotational direction (e.g., clockwise) with the exterior threaded portion 164 partially engaged with the interior threaded bore 138 of the collet 130 to cause the plug 160 to move in a first axial direction relative to the collet 130, as described in further detail herein. Conversely, the tool can engage the socket 166 and rotate in a second rotational direction (e.g., counterclockwise) to cause the plug 160 to move in a second axial direction relative to the collet 130). In some implementations, the socket 166 includes a torx head or a hex head.

Referring to FIG. 7C, in some implementations, the plug 160 optionally includes a fastener portion 168 that extends from the tip portion 162. The fastener portion 168 can be unitary and/or monolithic with the tip portion 162 or coupled to the tip portion 162 (e.g., via a welded connection, via a threaded connection to an interior threaded bore of the plug 160, or both). The fastener portion 168 is the same as, or similar to, the fastener 170A (FIG. 8) described below but excludes the head 172A. In an assembled configuration of the glenoid implant 100 (FIG. 1A-1B), the fastener portion 168 extends through the interior threaded bore 138 of the collet 130 and is generally used to engage bone of the patient (e.g., a portion of the scapula) in the same or similar manner as the plurality of fasteners 170A-170D described herein to aid in securing the glenoid implant 100 to the scapula of the patient. That is, the fastener portion 168 of the plug 160 can be used for central fixation of the glenoid implant 100.

Figure 8:
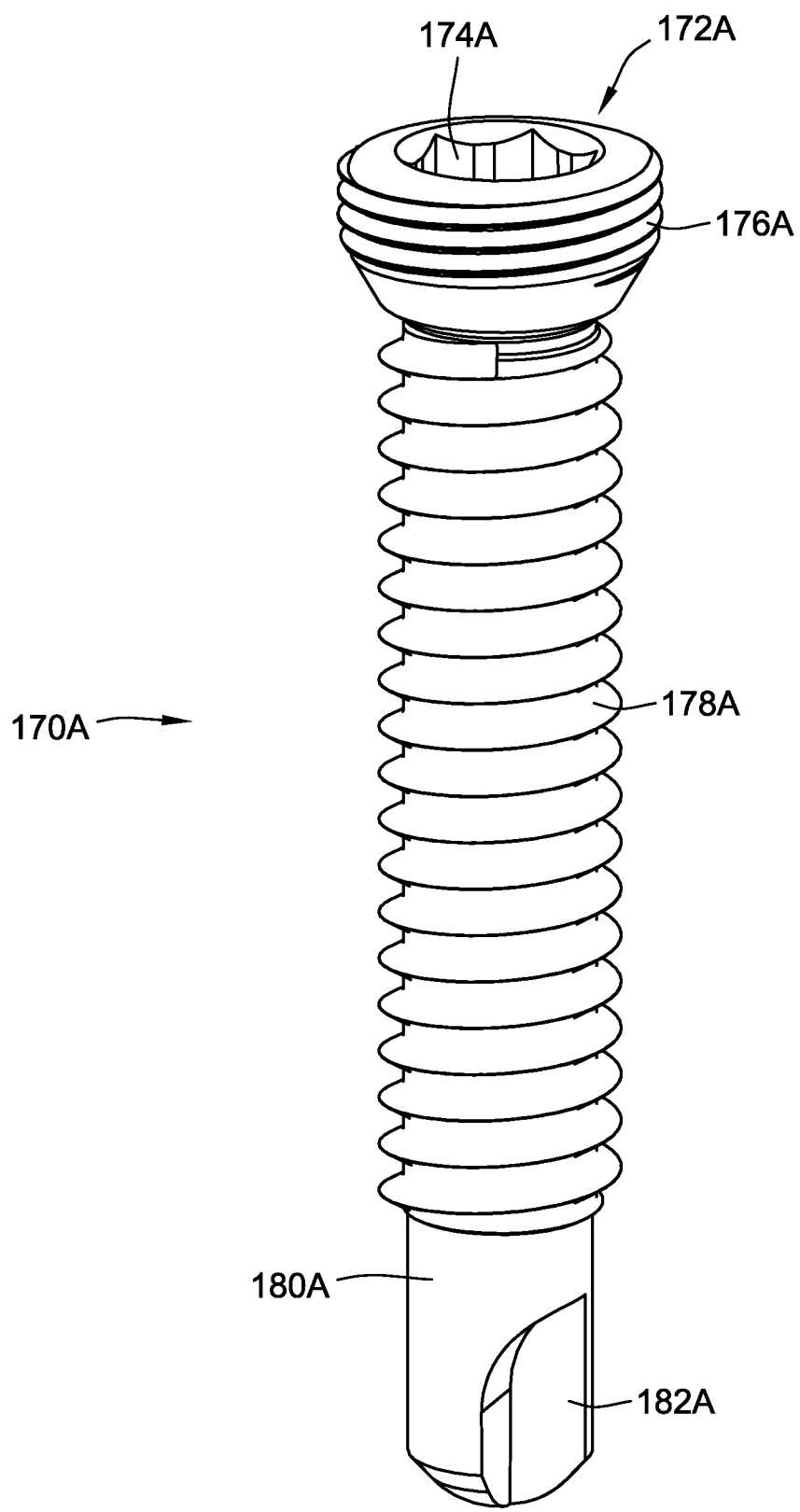
FIG. 8 is a perspective view of a fastener of the glenoid implant of FIGS. 1A-2, according to some implementations of the present disclosure.

Referring to FIG. 8, a first fastener 170A of the plurality of fasteners 170A-170D (FIGS. 1A-2) is illustrated. The first fastener 170A includes a head 172A, a threaded shaft portion 178A, and an unthreaded shaft portion 180A. Each of the other fasteners 170B-170D (FIGS. 1A-2) include a head, a threaded shaft portion, and unthreaded shaft portion that are the same as, or similar to, the head 172A, the threaded shaft portion 178A, and the unthreaded shaft portion 180A of the first fastener 170A (FIG. 7).

The head 172A of the first fastener 170A includes a socket 174A and a threaded portion 176A. The threaded portion 176A threadingly engages a corresponding one of the plurality of apertures 115A-115D of the plate 114 of the body 110 (FIGS. 3A-3B) to aid in securing the first fastener 170A to the plate 114 of the body 110. The socket 174A receives a portion of a tool therein that engages the socket 174A to rotate the first fastener 170A and cause axial movement of the first fastener 170A relative to the body 110. In some implementations, the socket 174A is the same as the socket 166 (FIG. 6A) of the plug 160. In other implementations, the socket 174A of the first fastener 170A (FIG. 7) is different than the socket 166 of the plug 160 (FIG. 6A), in which case different tools are used (e.g., the socket 166 is a torx head and the socket 174A is a hex head).

The threaded shaft portion 178A threadingly engages a portion of the scapula of a patient to aid in securing the glenoid implant 100 (FIGS. 1A-1B) to the scapula. In some implementations, the threaded shaft portion 178A includes self-tapping threads. The unthreaded shaft portion 180A includes a flute 182A. The flute 182A aids in cutting into the bone of the patient when installing the fastener 170A.

While the glenoid implant 100 is shown and described herein as having four fasteners 170A-170D, more generally, the glenoid implant 100 can have any suitable number of fasteners (e.g., one fastener, three fasteners, six fasteners, etc.). Similarly, while the plate 114 of the body 110 (FIGS. 3A-3B) is shown as having four apertures 115A-115D corresponding to the plurality of fasteners 170A-170D, the plate 114 can have any number of apertures corresponding to the number of fasteners.

Referring generally to FIGS. 9A-11B, the glenoid implant 100 can be installed in a portion of a bone B of a patient (e.g., a scapula). As described in further detail herein, the installed glenoid implant 100 can be used for an anatomic shoulder replacement procedure or a reverse shoulder replacement surgery.

Figure 9A:
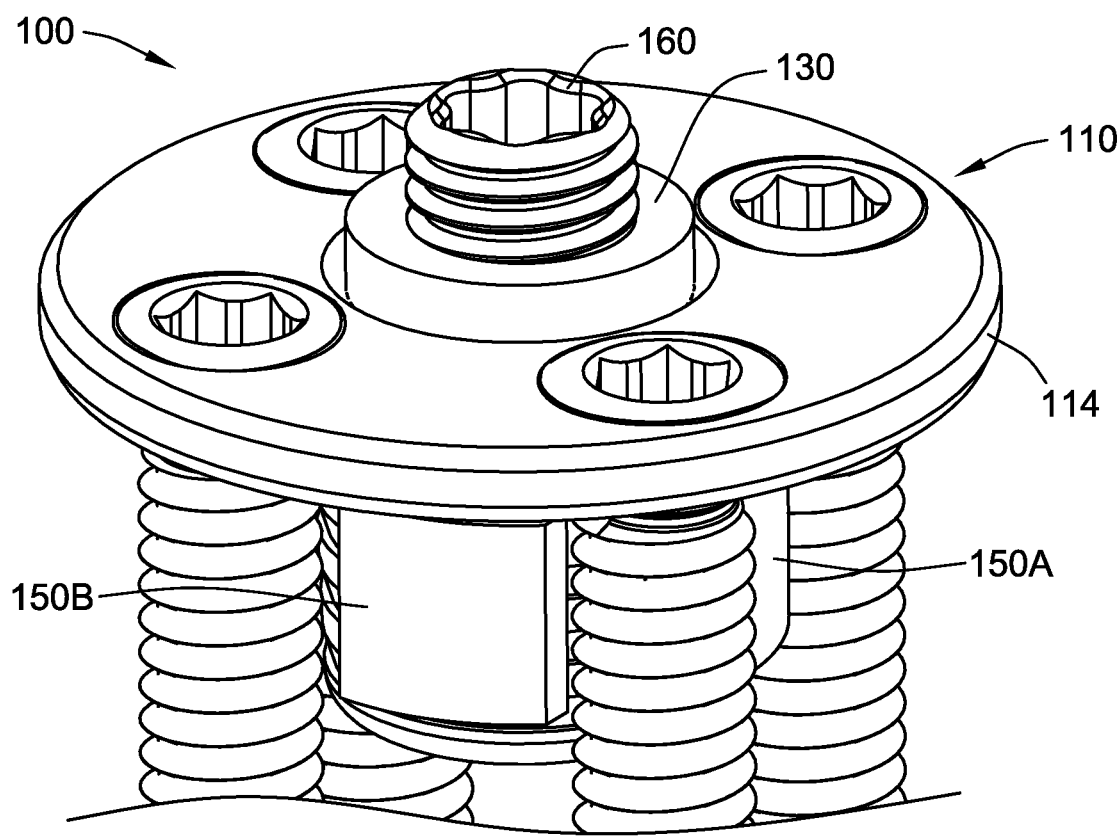
FIG. 9A is a partial perspective view of the glenoid implant of FIG. 1A with a plug in a first axial position and a plurality of fins in a first generally inward position, according to some implementations of the present disclosure.
Figure 9B:
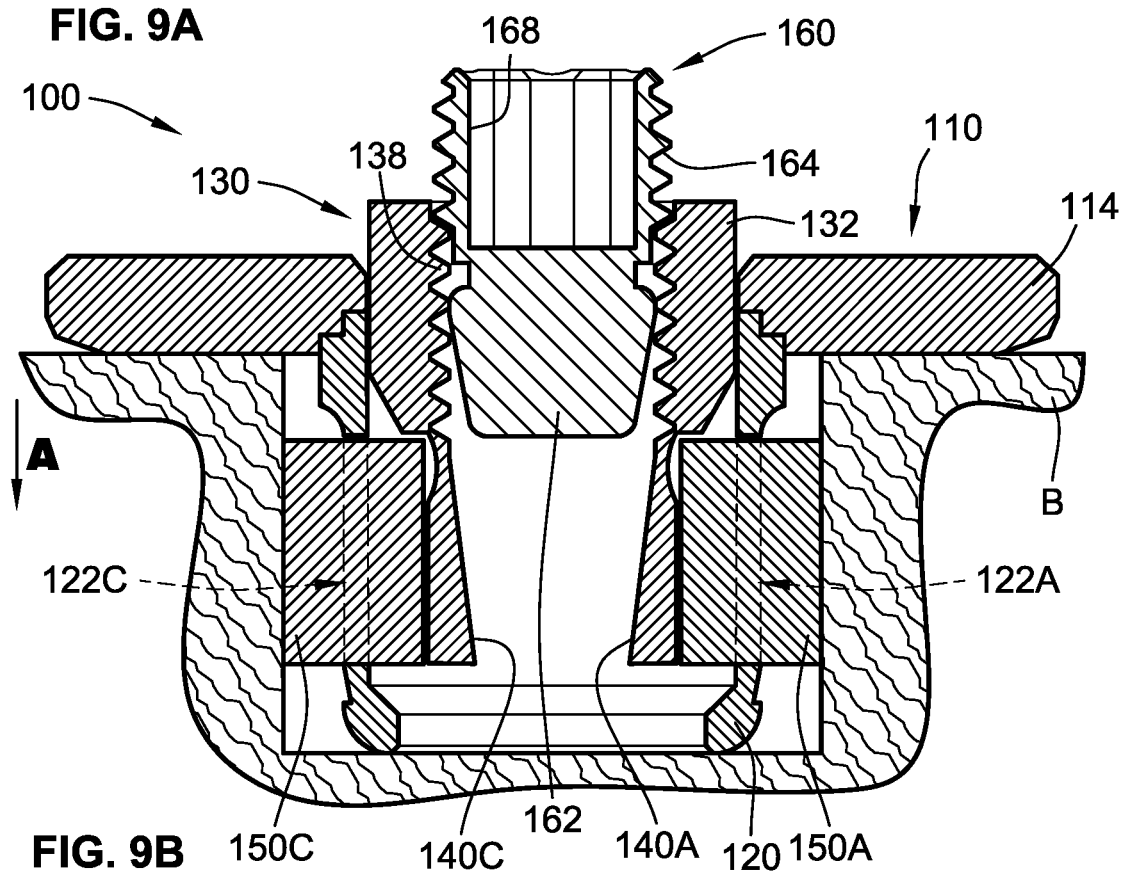
FIG. 9B is a partial cross-sectional view of the glenoid implant of FIG. 1A with the plug in the first axial position and the plurality of fins in the first generally inward position, according to some implementations of the present disclosure.

Referring to FIGS. 9A and 9B, the plug 160 of the glenoid implant 100 is in a first axial position relative to the body 110 and the collet 130, and the plurality of fins 150A-150D are in a first generally inward position. As shown in FIG. 9B, at least a portion of the glenoid implant 100 is received within a cavity formed in the bone B (e.g., scapula), including the plurality of fins 150A-150D, a portion of the collet 130 that includes at least the plurality of deflectable arms 140A-140D, and a portion of the boss 120 that includes at least the plurality of slots 122A-122D. The outer diameter of the plate 114 is greater than an outer diameter of the cavity in the bone B to prevent the entire glenoid implant 100 from falling into the opening or hole.

In the first generally inward position (FIG. 9B), the plurality of fins 150A-150D are generally flush with and spaced from (e.g., by less than 0.5 millimeters, by less than 1 millimeters, etc.) the edges of the cavity in the bone B such that the boss 120 of the body 110 of the glenoid implant 100 can be received within the cavity in the bone B. That is, in the first generally inward position (FIG. 9B), the plurality of fins 150A-150D do not protrude into the bone material lining the cavity in the bone B.

As described herein, the socket 166 of the plug 160 can be engaged by a tool to rotate the plug 160 relative to the collet 130. Because the exterior threaded portion 164 of the plug 160 is threadingly engaged with the interior threaded bore 138 of the collet 130, rotation of the plug 160 (e.g., by a tool that engages the socket 166) causes axial movement of the plug 160 in the direction of arrow A (FIG. 9B).

Figure 10A:
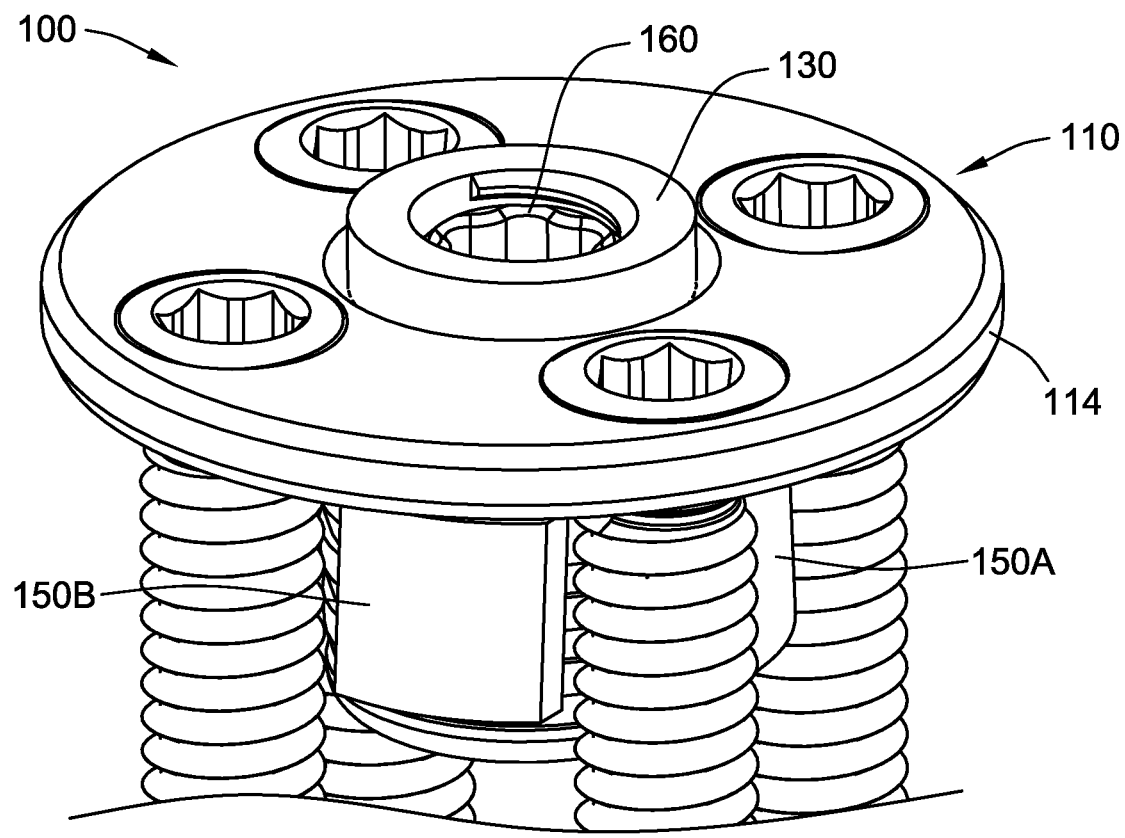
FIG. 10A is a partial perspective view of the glenoid implant of FIG. 1A with the plug in a second axial position, according to some implementations of the present disclosure.
Figure 10B:
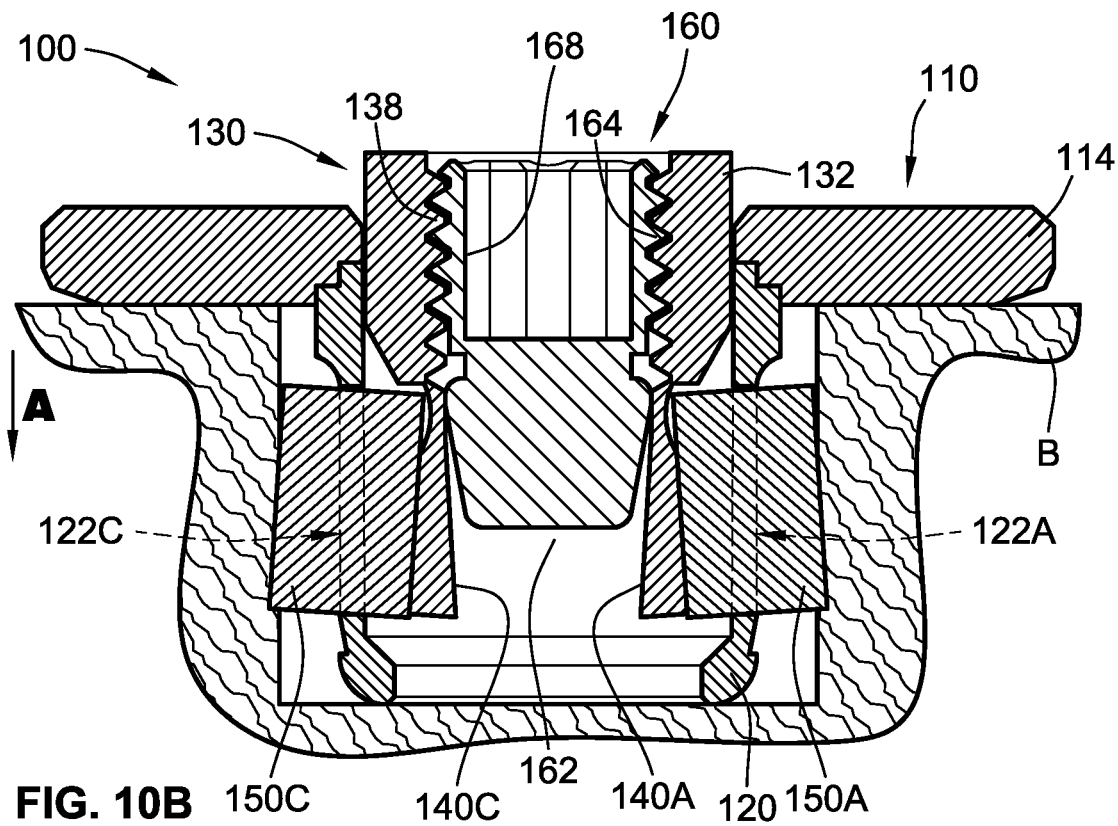
FIG. 10B is a partial cross-sectional view of the glenoid implant of FIG. 1A with the plug in the second axial position, according to some implementations of the present disclosure

Referring now to FIGS. 10A and 10B, responsive to rotation of the plug 160, the plug 160 moves to a second axial position relative to the body 110 and the collet 130, and the plurality of fins 150A-150D move from the first generally inward position (FIG. 9B). As shown by a comparison between FIG. 9B and FIG. 10B, the plug 160 moves in the direction of arrow A responsive to rotation (e.g., by a tool) such that the tip portion 162 of the plug 160 engages the plurality of deflectable arms 140A-140D of the collet 130, causing the each of the plurality of deflectable arms 140A-140D to move radially outward relative to the rest of the collet 130 and a central axis of the glenoid implant 100. In turn, the radially outward movement of the plurality of deflectable arms 140A-140D causes radially outward movement of the plurality of fins 150A-150D away from the first generally inward position (FIG. 9B) towards a second generally outward position (FIG. 11B). In this manner, the tip portion 162 of the plug 160 indirectly engages the plurality of fins 150A-150B when moving in the direction of arrow A, while the plurality of deflectable arms 140A-140D directly engage corresponding ones of the plurality of fins 150A-150D. As shown in FIG. 10B, movement of the plug 160 in the direction of arrow A causes the plurality of fins 150A-150D to engage or contact the outer edges of the cavity in the bone B (e.g., spongey bone material).

Figure 11A:
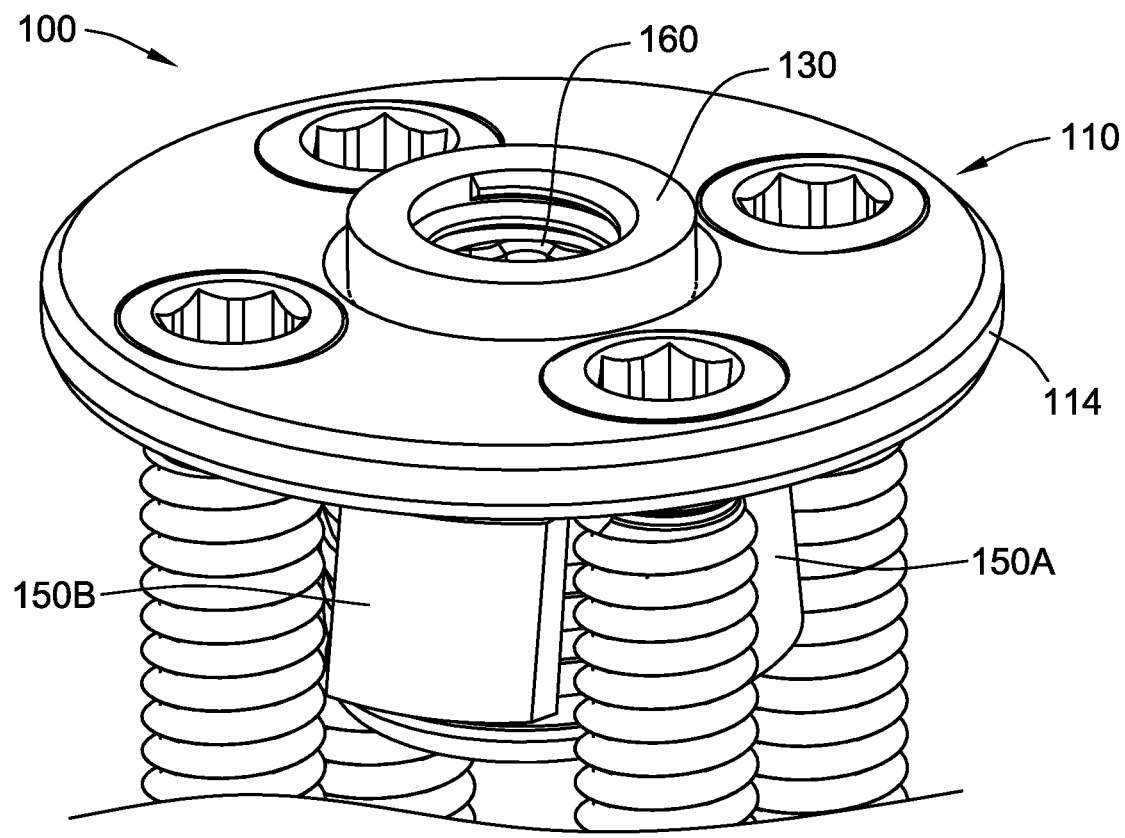
FIG. 11A is a partial perspective view of the glenoid implant of FIG. 1A with the plug in a third axial position and the plurality of fins in a second generally outward position, according to some implementations of the present disclosure.
Figure 11B:
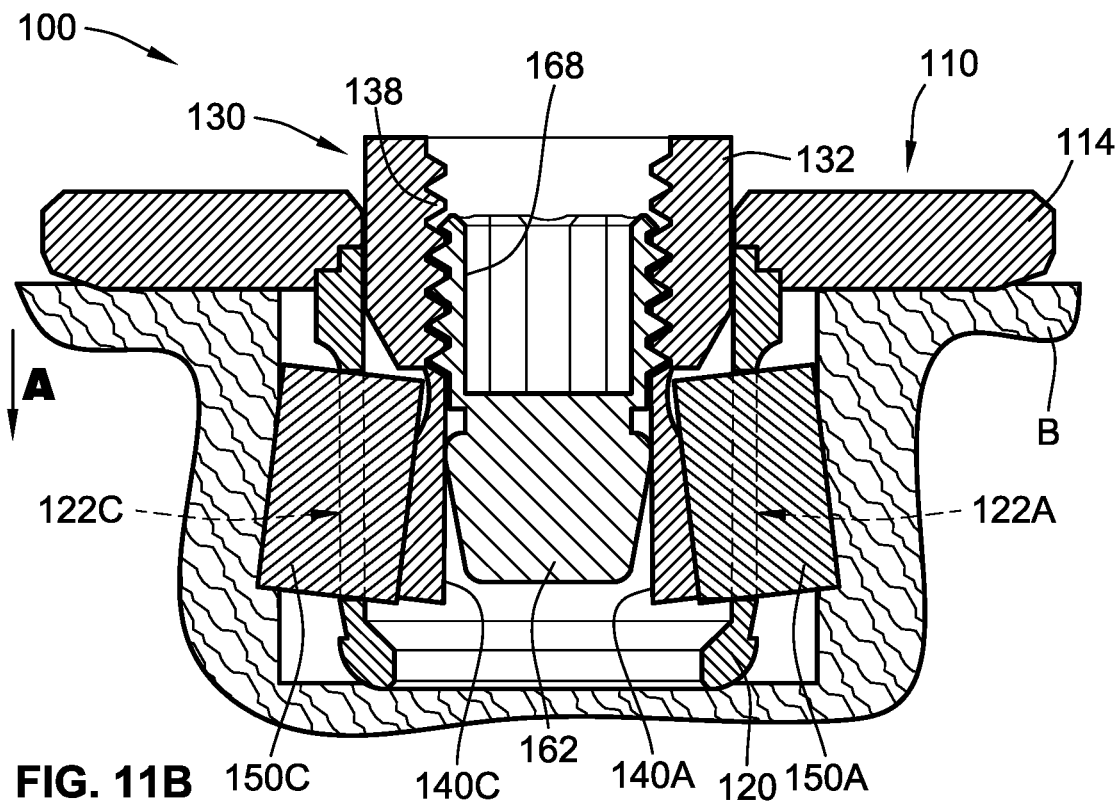
FIG. 11B is a partial cross-sectional view of the glenoid implant of FIG. 1A with the plug in the third axial position and the plurality of fins in the second generally outward position, according to some implementations of the present disclosure

Referring to FIGS. 11A and 11B, responsive to continued rotation of the plug 160, the plug 160 moves to a third axial position relative to the body 110 and the collet 130 and the plurality of fins 150A-150D move to a second generally outward position relative to the body 110. As shown by a comparison between FIG. 11B and FIG. 10B, continued movement of the plug 160 in the direction of arrow A causes the tip portion 162 to cause further radially outward movement of the plurality of deflectable arms 140A-140D of the collet 130 relative to the rest of the collet 130 and a central axis of the glenoid implant 100. In turn, each of the plurality of deflectable arms 140A-140D cause correspond corresponding ones of the plurality of fins 150A-150D to move to the second generally outward position (FIG. 11B) relative to the body 110.

In the second generally outward position (FIG. 11B), the plurality of fins 150A-150D engage and protrude into the edges of the bone (e.g., spongey bone material) defining the cavity in the bone B. The engagement between the plurality of fins 150A-150D and the bone material aids in securing the glenoid implant 100 to the bone B and/or promotes osseointegration of the glenoid implant 100.

Because each of the plurality of deflectable arms 140A-140D have an inwardly tapered inner surface (FIGS. 4A-4B) that engage the tip portion 162 of the plug 160 when the plug 160 moves in the direction of arrow A, each of the plurality of fins 150A-150D engage and protrude into the spongy bone material at an angle (e.g., between about 1 degree and about 25 degrees). That is, the plurality of fins 150A-150D move both horizontally into the bone material and vertically in the opposite direction of arrow A. As shown by a comparison between FIG. 9B and FIG. 11B, moving the plurality of fins 150A-150D to the second generally outward position pulls the plate 114 down in the direction of arrow A due to the angle at which the plurality of fins 150A-150D contact the spongy bone of the opening in the bone B, further aiding in securing the glenoid implant 100 to the bone B.

Each of the plurality of fins 150A-150D move by a predetermined distance between the first generally inward position (FIG. 9B) and the second generally outward position (FIG. 11B). The predetermined distance can be, for example, between about 0.5 millimeters and about 1.5 millimeters, between about 0.25 millimeters and about 2.5 millimeters, between about 0.1 millimeters and about 3 millimeters, etc. Preferably, the predetermined distance is between about 0.5 millimeters and about 1.5 millimeters. In this manner, the overall diameter of the portion of the glenoid implant 100 that is positioned in the opening in the bone B can increase by between about 1 millimeter and about 3 millimeters to aid in securing the glenoid implant 100 to the bone (e.g., scapula).

As shown in FIGS. 9A and 9B, when the plurality of fins 150A-150D are in the first generally inward position, a portion of the exterior threaded portion 164 of the plug 160 protrudes from the collet 130, while the tip portion 162 of the plug 160 is completely disposed within the interior threaded bore 138 of the collet 130. By contrast, as shown in FIGS. 11A and 11B, when the plurality of fins 150A-150D are in the second generally outward position, the entire exterior threaded portion 164 of the plug 160 is disposed within the interior threaded bore 138 of the collet 130. Alternatively, in some implementations, an upper surface or edge of the plug 160 can be generally flush with an upper surface or edge of the collet 130 when the plurality of fins 150A-150D are in the second generally outward position (FIG. 11B). Alternatively still, in other implementations, a portion of the exterior threaded portion 164 of the plug 160 can protrude from the collet 130 even when the plurality of fins 150A-150D are in the second generally outward position (FIG. 11B).

Figure 12:
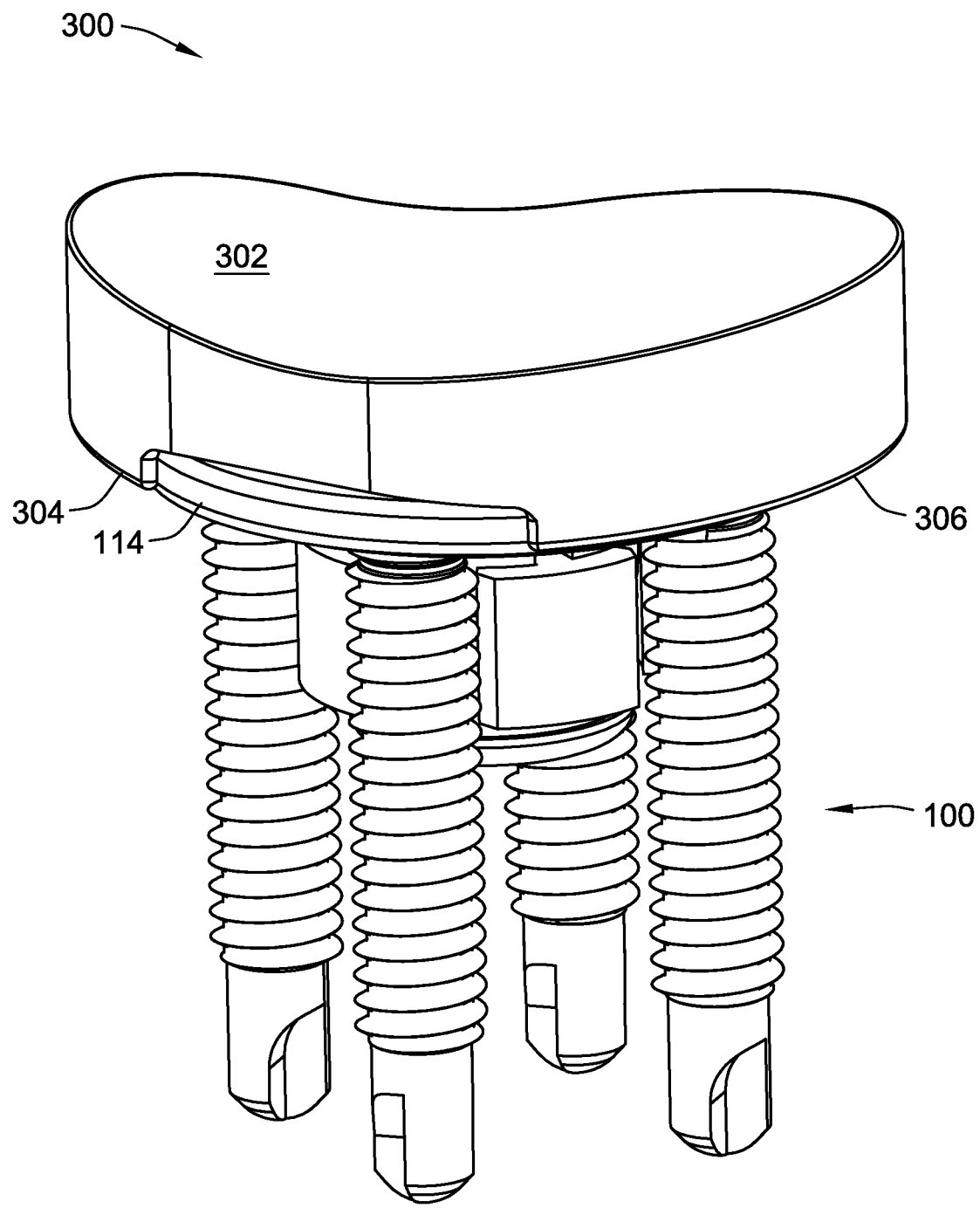
FIG. 12 is a perspective view of the glenoid implant of FIG. 1A coupled to a glenoid component, according to some implementations of the present disclosure.
Figure 13:
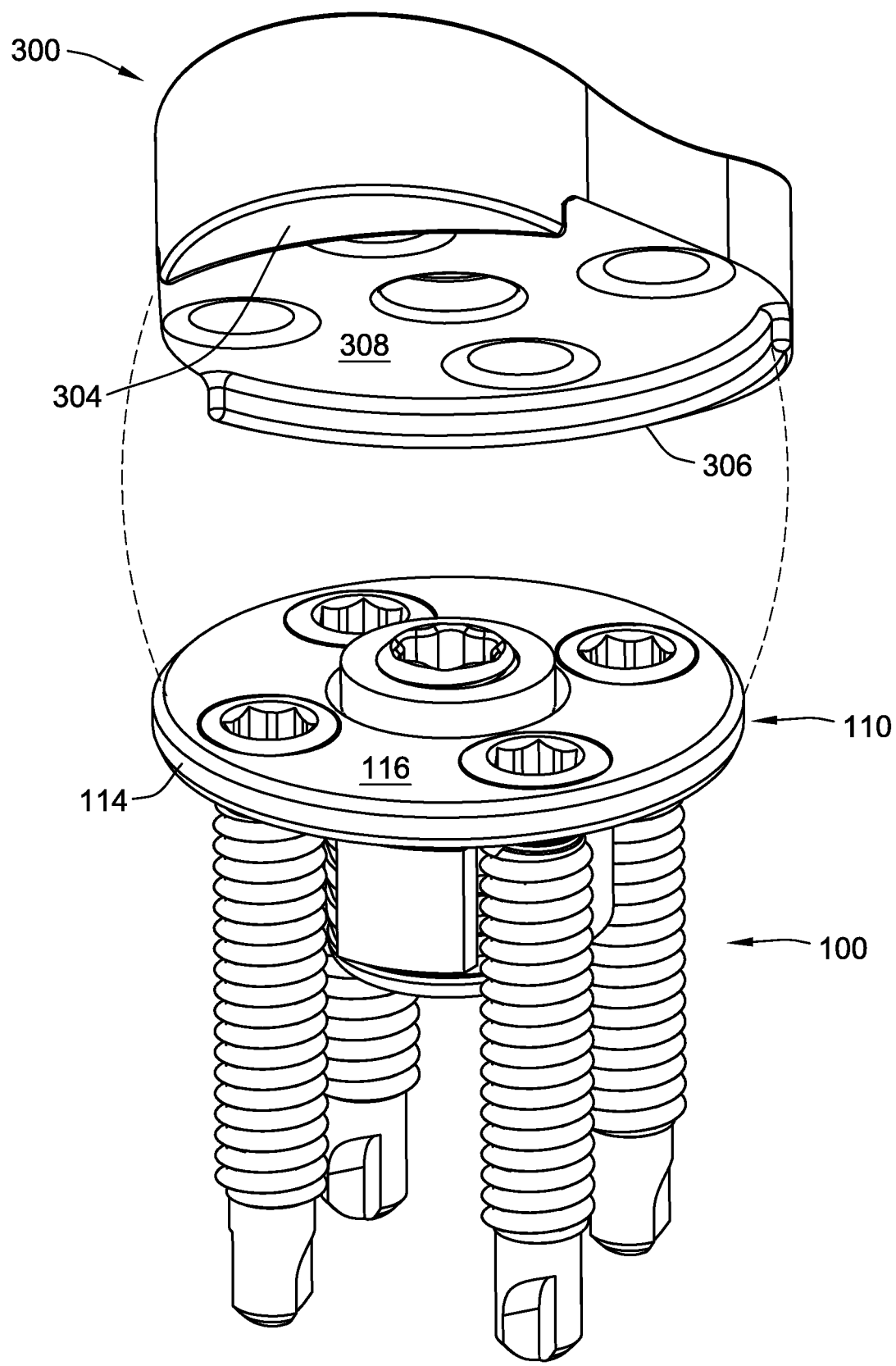
FIG. 13 is an exploded view of the glenoid implant and glenoid component of FIG. 12A, according to some implementations of the present disclosure.

Referring to FIGS. 12 and 13, in some implementations, the glenoid implant 100 described herein (FIGS. 1A-11B) can be used for an anatomic shoulder replacement procedure (TSA). Anatomic shoulder replacement procedures involve repairing or replacing the affected extremity's (e.g., shoulder) ball and socket joint after years of degeneration. The ball portion of the shoulder (also referred to as a humeral head) is replaced with a metal sphere, while a plastic or other synthetic insert is used to replace the socket. This type of procedure is most helpful for patients with arthritis and other related conditions, which result in joint problems and missing cartilage.

In such implementations, a glenoid component 300 is coupled to the glenoid implant 100. In some implementations, the glenoid component 300 is referred to as an anatomic glenoid insert component. The glenoid component 300 has a general pear-like shape and is configured to engage with a spherical or ball-shaped humeral component (e.g., implanted in a humerus bone of the patient) to allow rotation of the shoulder. More specifically, the glenoid component 300 includes a curved outer surface 302 that acts as a socket for the metal sphere that replaces the humeral head to permit rotation.

The glenoid component 300 also includes a first rim portion 304 and a second rim portion 306 that protrude from a lower surface 308 (FIG. 13) for coupling the glenoid component 300 to the glenoid implant 100. More specifically, the first rim portion 304 and the second rim portion 306 form a press fit or snap fit connection with the plate 114 of the body 110 of the glenoid implant 100 such that the lower surface 308 of the glenoid component 300 contacts the upper surface 116 of the plate 114 so that the glenoid component 300 is secured to the glenoid implant 100 (which in turn is secured to the scapula of the patient as described above).

Figure 14:
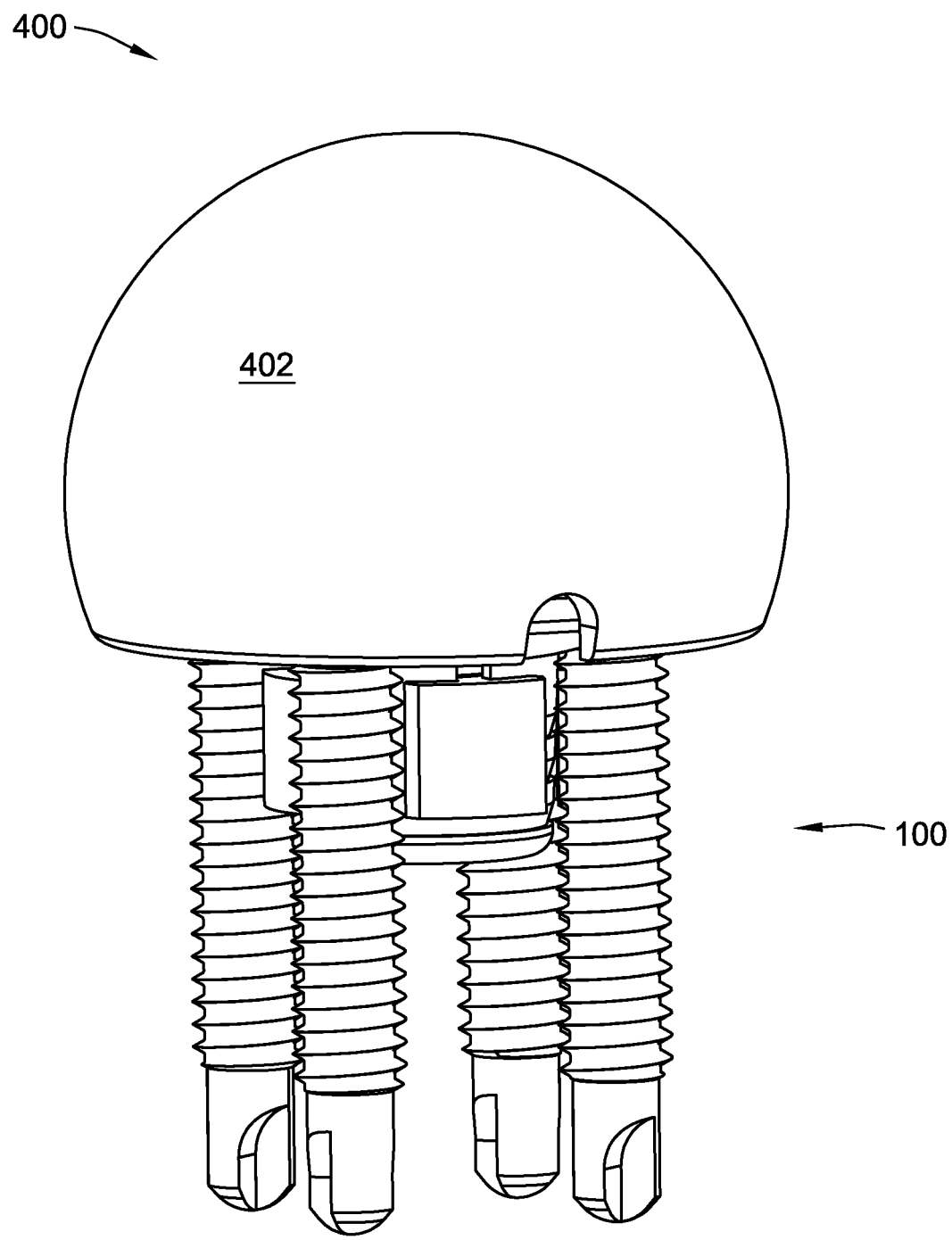
FIG. 14 is a perspective view of the glenoid implant of FIG. 1A coupled to a glenosphere, according to some implementations of the present disclosure.
Figure 15:
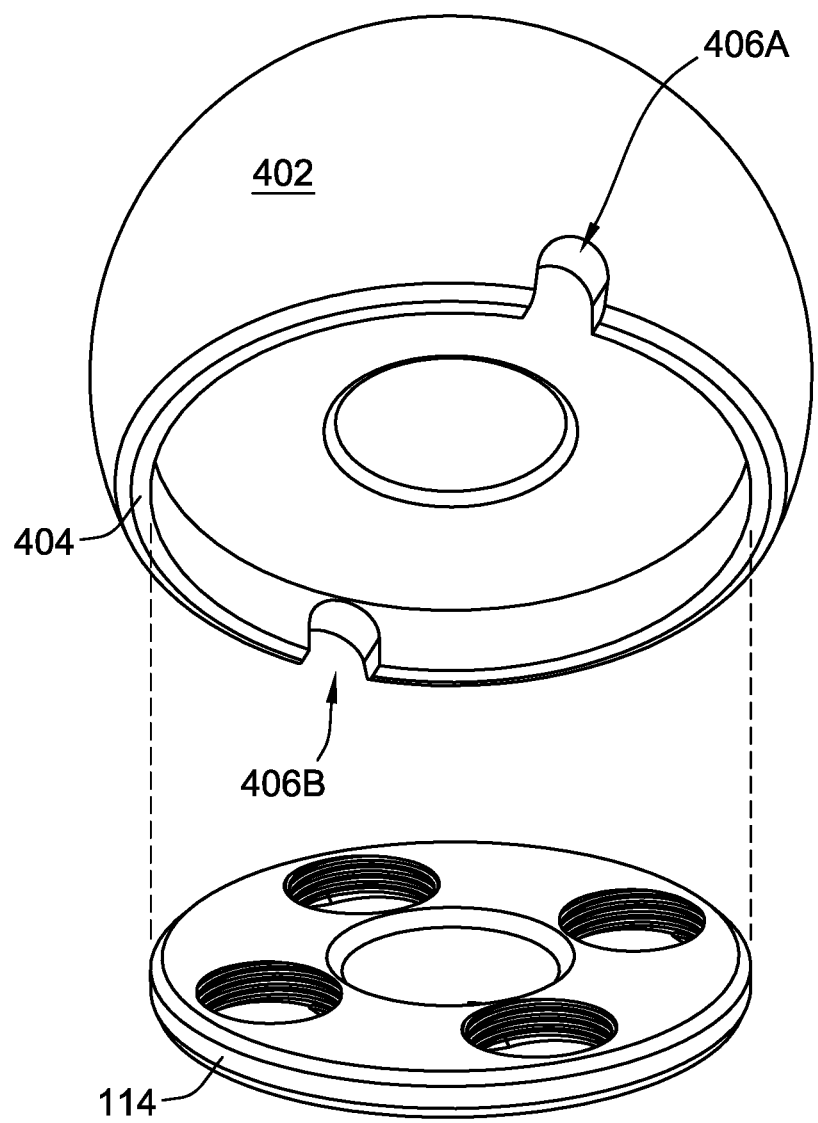
FIG. 15 is a partial exploded view of the glenoid implant and glenosphere of FIG. 14, according to some implementations of the present disclosure.

Referring to FIGS. 14 and 15, in some implementations, the glenoid implant 100 described herein (FIGS. 1A-11B) can be used for a reverse shoulder replacement procedure (RSA). The reverse should replacement procedure differs from an anatomic shoulder replacement procedure (FIGS. 12 and 13) in that the ball and socket arrangement is reversed. Reverse should replacement is often used for patients with large rotator cuff tears or arthritis, or arthropathy because the rotator cuff muscles no longer function. The reverse shoulder replacement relies on the deltoid muscle rather than the rotator cuff to position and power the arm.

In such implementations, a glenosphere 400 is coupled to the glenoid implant 100. The glenosphere 400 has a generally spherical or ball-like shape and engages a socket that is attached to the humerus bone of the patient. In some implementations, the glenosphere 400 can be referred to as a reverse glenosphere.

The glenosphere 400 includes a lower rim 404 that engages a portion of the plate 114 of the glenoid implant 100 (FIG. 15) to couple the glenosphere 400 the glenoid implant 100 via a press fit or snap fit connection. The glenosphere 400 also includes a pair of notches 406A-406B that aid in permitting the glenosphere 400 to flex or bend when fitting the glenosphere 400 onto the glenoid implant 100.

Referring generally to FIGS. 16-18C, a glenoid implant 500 according to some implementations of the present disclosure is illustrated. The glenoid implant 500 is similar to the glenoid implant 100 (FIGS. 1A-11B) in that the glenoid implant 500 includes a body 510, a plug 560, and a plurality of fasteners 570A-570D.

The body 510 is similar to the body 110 of the glenoid implant 100 (FIGS. 3A-3B) in that the body 510 of the glenoid implant 500 includes a plate 514 and a boss 520. The body 510 of the glenoid implant 500 differs from the body 110 of the glenoid implant 100 (FIGS. 3A-3B) in that the body 510 of the glenoid implant 500 includes an interior threaded bore 512 extending therethrough rather than an unthreaded central aperture. The body 510 of the glenoid implant 500 also differs from the body 110 of the glenoid implant 100 (FIGS. 3A-3B) in that the plate 114 and the boss 520 of the body 510 of the glenoid implant 500 are unitary and/or monolithic.

Figure 16:
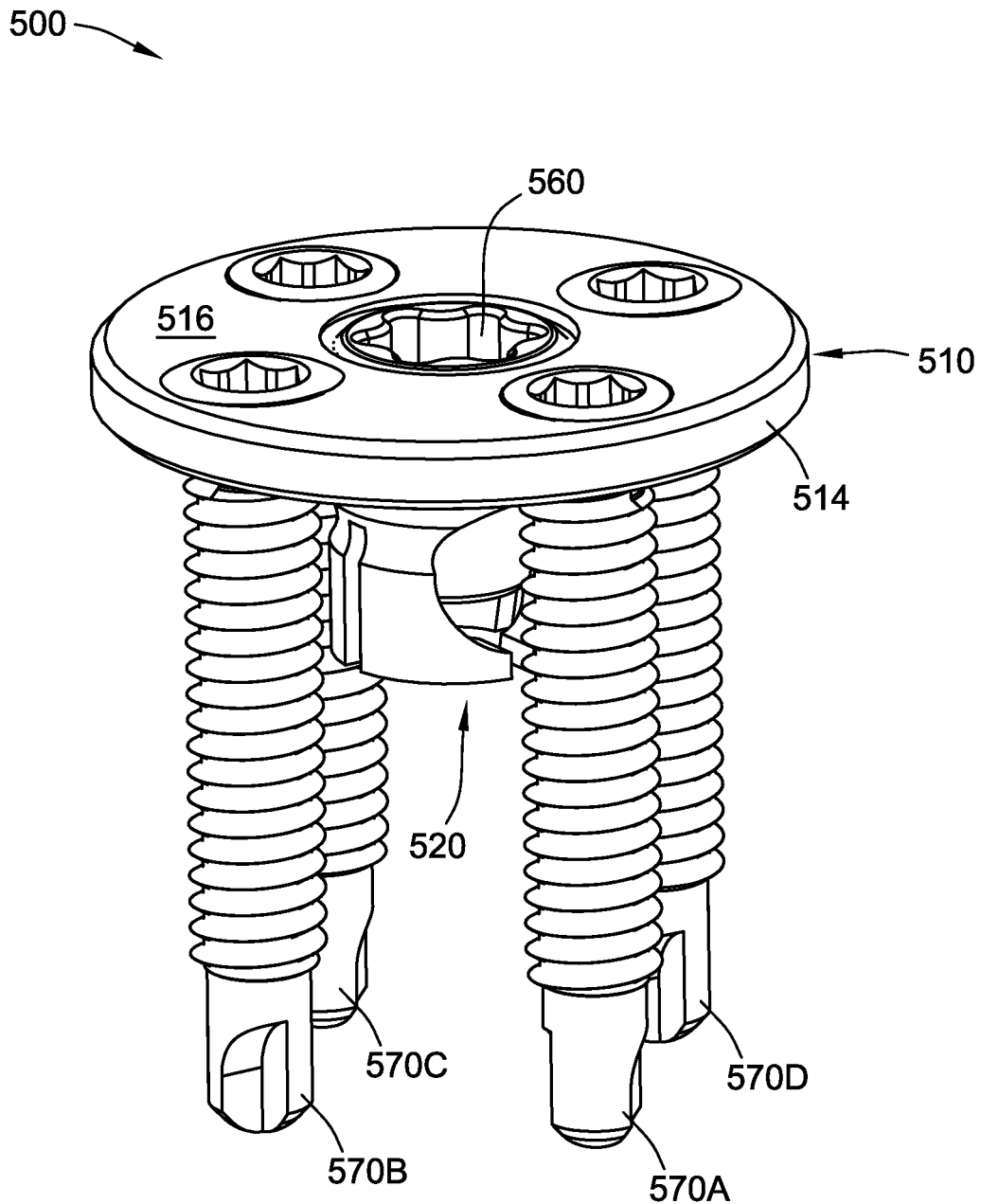
FIG. 16 is a perspective assembled view of a glenoid implant, according to some implementations of the present disclosure.
Figure 17A:
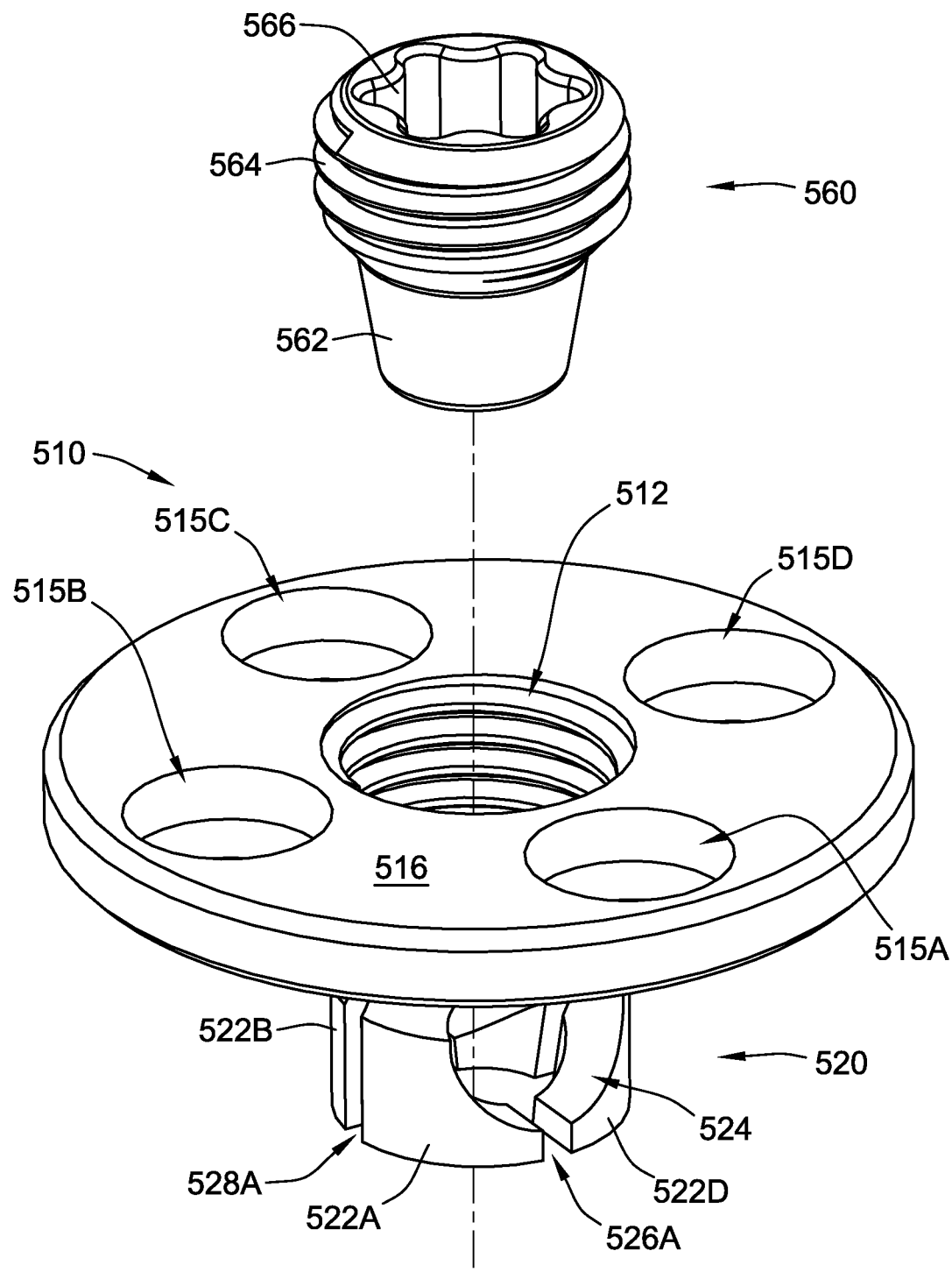
FIG. 17A is a first perspective exploded view of the glenoid implant of FIG. 16, according to some implementations of the present disclosure.
Figure 17B:
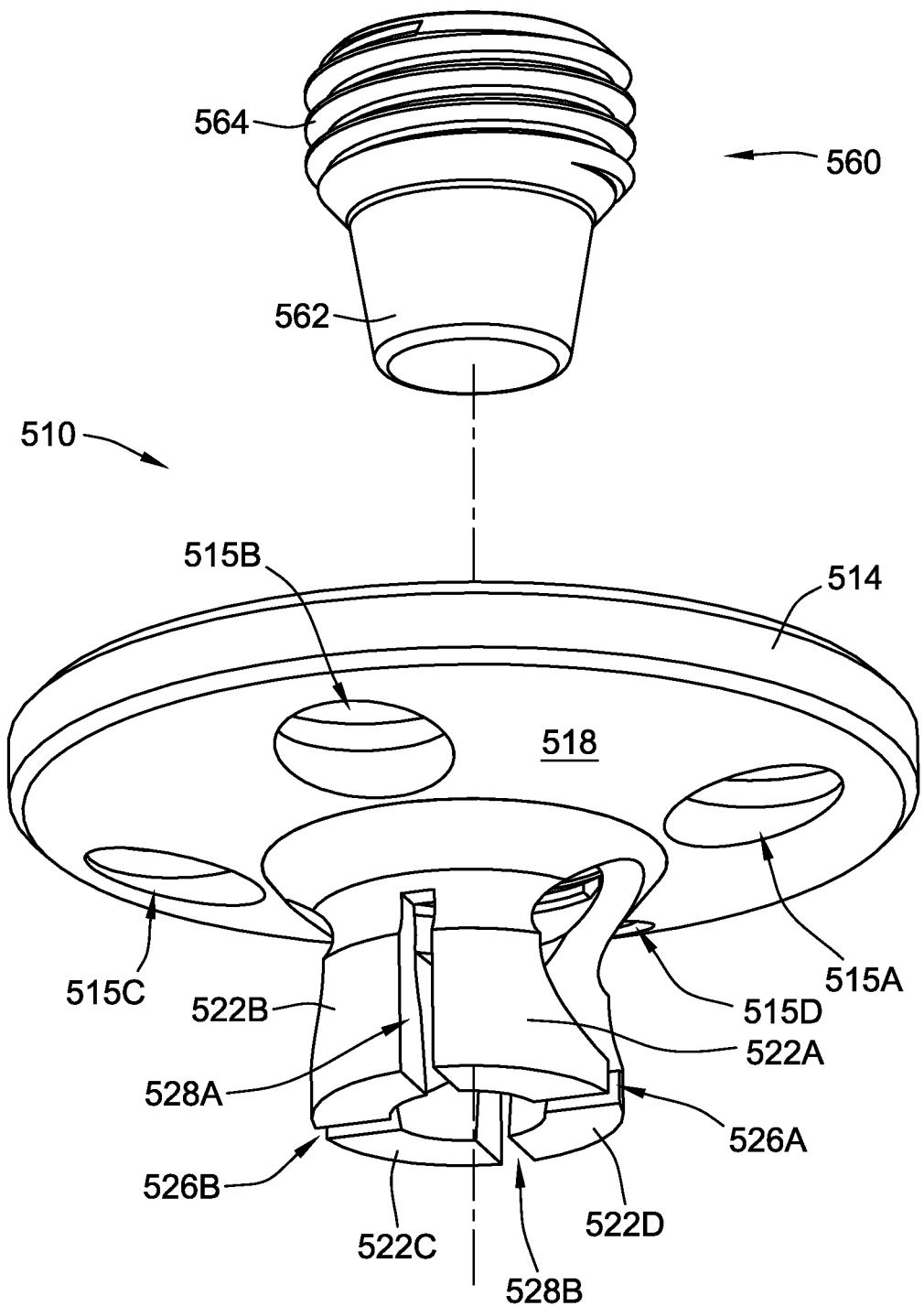
FIG. 17B is a second perspective exploded view of the glenoid implant of FIG. 16, according to some implementations of the present disclosure.

The plate 514 of the body 510 of the glenoid implant 500 is the same as, or similar to, the plate 114 of the body 110 of the glenoid implant 100 (FIGS. 3A-3B) described above and includes a plurality of apertures 515A-515D to receiving corresponding ones of the plurality of fasteners 570A-570D (FIG. 16), an upper surface 516 (FIG. 17A), and a lower surface 518 (FIG. 17B).

As shown in FIG. 17B, the boss 520 extends from the lower surface 518 of the plate 514. The boss 520 includes a plurality of deflectable portions 522A-522D that function in the same or similar manner as the plurality of fins 150A-150D of the glenoid implant 100 described herein. The plurality of deflectable portions 522A-522D are defined by a laterally extending aperture 524 in the boss 520, a pair of gaps 526A-526B, and a pair of slots 528A-528B. The laterally extending aperture 524 extends along an axis that is generally orthogonal or perpendicular to an axis along which the interior threaded bore 512 (FIG. 17A) of the body 510 extends. The laterally extending aperture, the pair of gaps 526A-526B, and the pair of slots 528A-528B permit the plurality of deflectable portions 522A-522D to move relative to the rest of the body 510 between a first generally inward position and a second generally outward position, as described below.

Referring to FIGS. 17A and 17B, the plug 560 of the glenoid implant 500 is the same as, or similar to, the plug 160 (FIGS. 7A-7B) of the glenoid implant 100 and includes a tip portion 562, an exterior threaded portion 564, and a socket 566. The exterior threaded portion 564 threadingly engages the interior threaded bore 512 of the body 510 when the glenoid implant 500 is in an assembled configuration (FIG. 16). The socket 566 engages a tool that rotates the plug 560 relative to the body 510. In some implementations, the plug 560 also includes a threaded shaft portion extending from the tip portion 562 that is the same as or similar to the fastener portion 168 of the plug 160 of the glenoid implant 100 (FIG. 7C).

Referring back to FIG. 16, the plurality of fasteners 570A-570D (FIG. 16) of the glenoid implant 500 are the same as, or similar to, the plurality of fasteners 170A-170D of the glenoid implant 100 (FIGS. 1A-1B and FIG. 8).

Figure 18A:
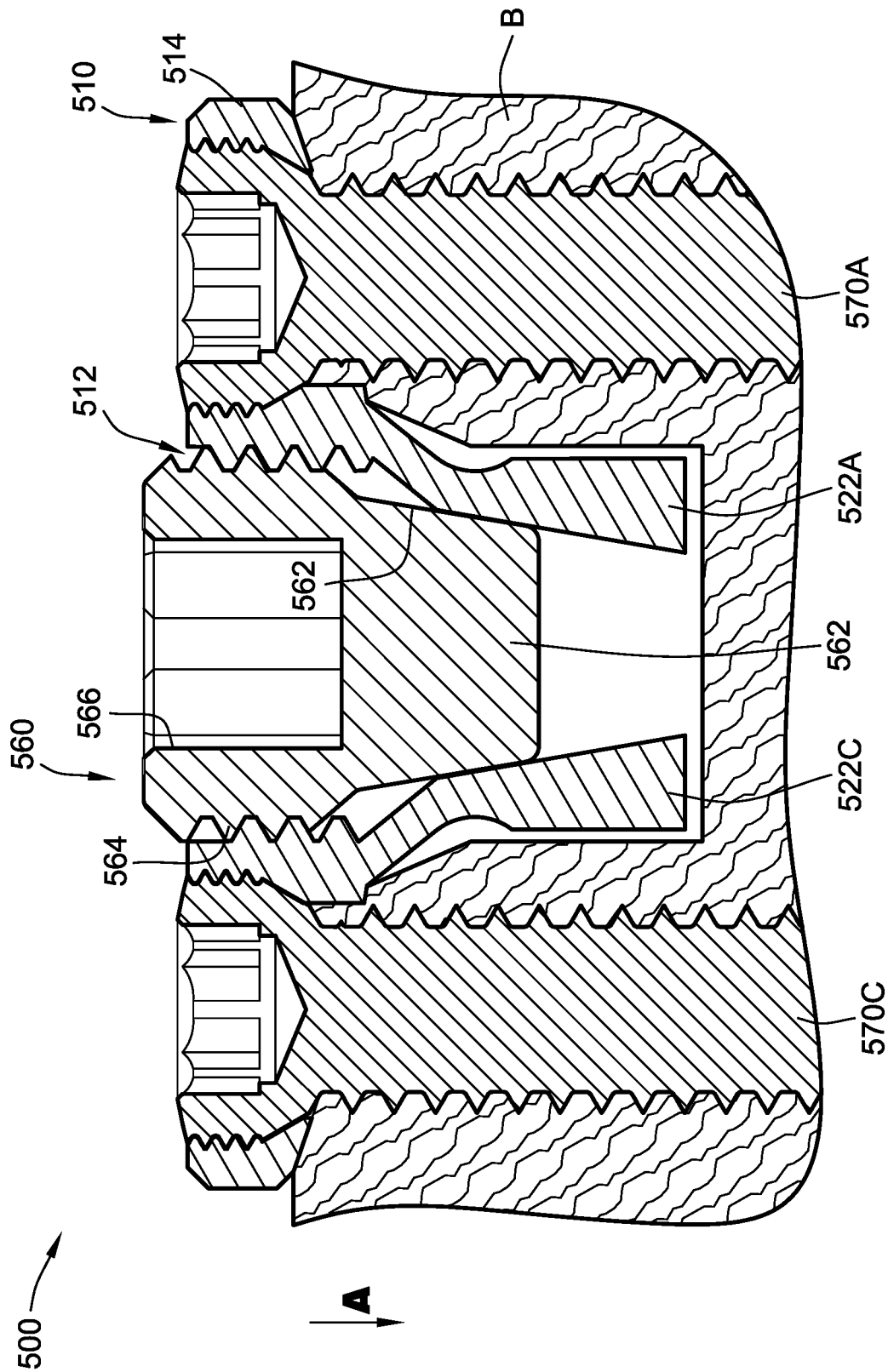
FIG. 18A is a first cross-sectional view of the glenoid implant of FIG. 16 with a plurality of deflectable portions in a first generally inward position, according to some implementations of the present disclosure.
Figure 18B:
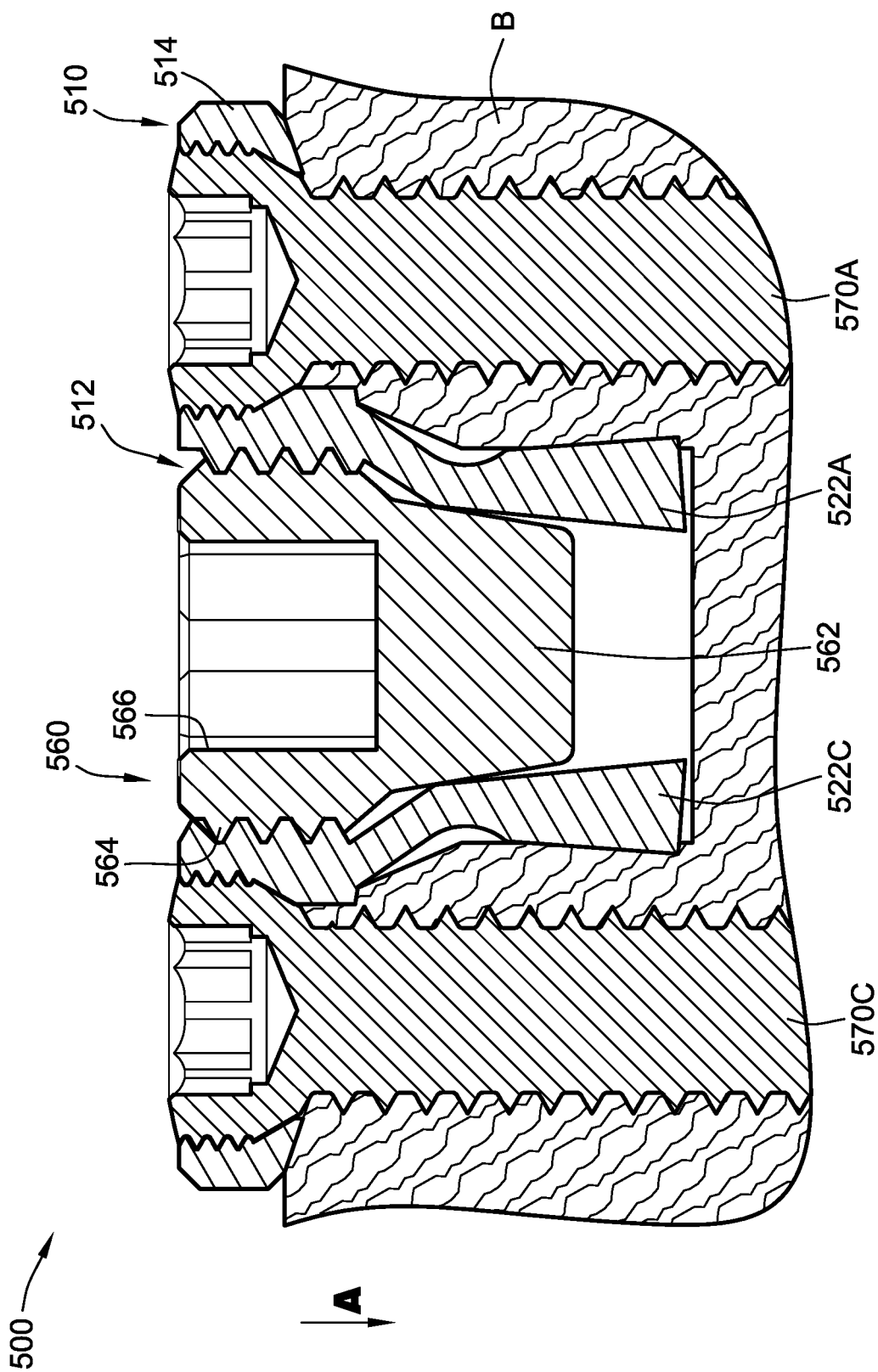
FIG. 18B is a second cross-sectional view of the glenoid implant of FIG. 16 with the plurality of deflectable portions moved away from the first generally inward position of FIG. 18A, according to some implementations of the present disclosure.
Figure 18C:
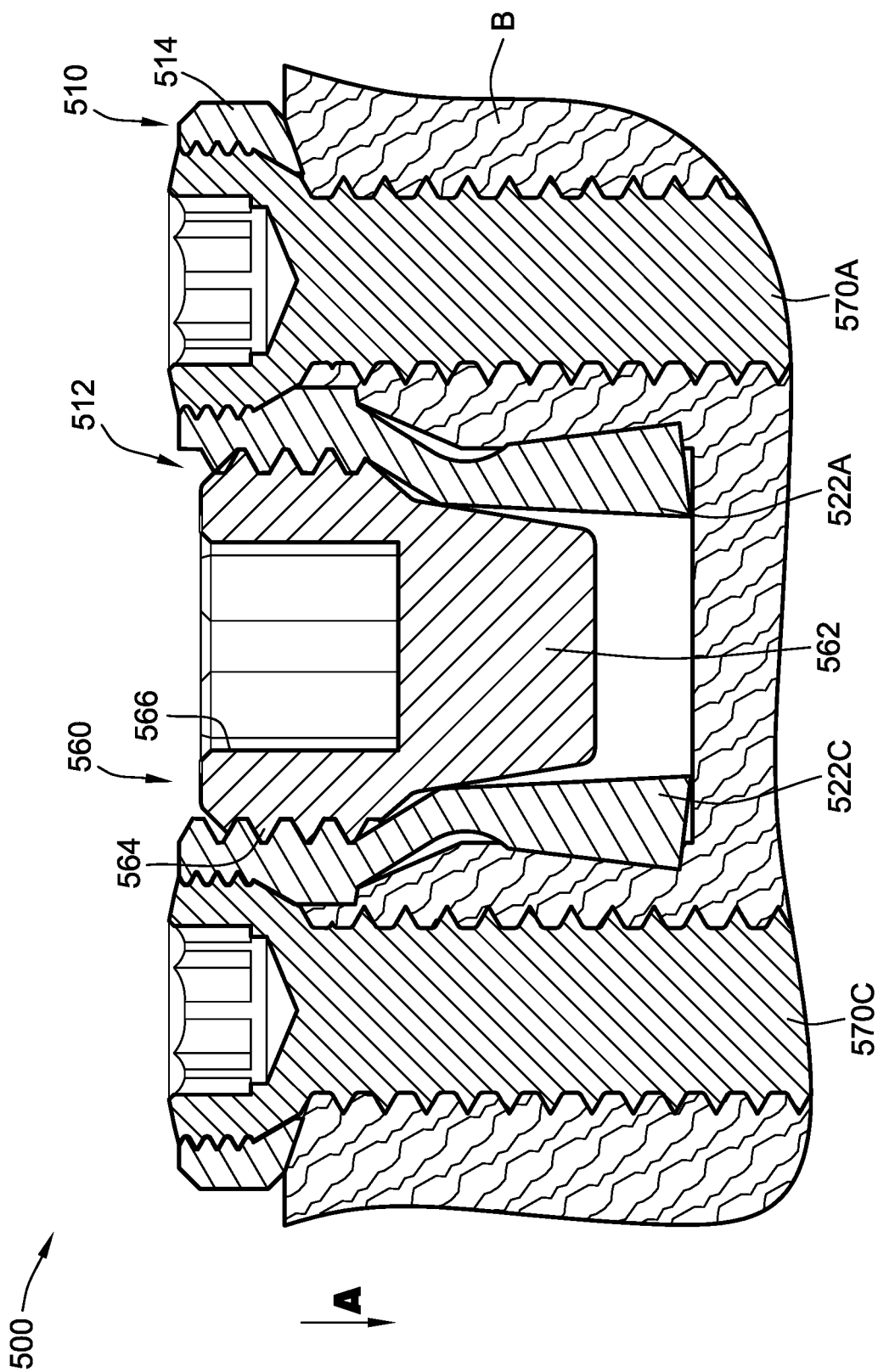
FIG. 18C is a third cross-sectional view of the glenoid implant of FIG. 16 with the plurality of deflectable portions in a second generally outward position, according to some implementations of the present disclosure.

Referring to FIGS. 18A-18C, the glenoid implant 500 can be installed in a portion (e.g., cavity) of a bone B of a patient. As described in further detail herein, the installed glenoid implant 500 can be used for an anatomic shoulder replacement procedure or a reverse shoulder replacement surgery.

Referring to FIG. 18A, the glenoid implant 500 is positioned in a cavity in a bone B of a patient. More specifically, the boss 520, a portion of the plate 514, and a portion of the plug 560 are positioned within the cavity. As shown, the plug 560 of the glenoid implant 500 is in a first axial position relative to the body 510 and the plurality of deflectable portions 522A-522D are in a first generally inward position. The outer diameter of the plate 514 is greater than an outer diameter of the cavity in the bone B to prevent the entire glenoid implant 500 from falling into the opening or hole.

In the first generally inward position (FIG. 18A), the plurality of deflectable portions 522A-522D are generally flush with or spaced from (e.g., by less than 0.5 millimeters, by less than 1 millimeter, etc.) the edges of the cavity in the bone B such that the boss 520 of the body 510 of the glenoid implant 500 can be received within the cavity in the bone B. That is, in the first generally inward position (FIG. 18A), the plurality of deflectable portions 522A-522D do not protrude into the bone material lining the cavity in the bone B.

As described herein, the socket 566 of the plug 560 can be engaged by a tool to rotate the plug 560 relative to the body 510. Because the exterior threaded portion 564 of the plug 560 is threadingly engaged with the interior threaded bore 512 of the body 510, rotation of the plug 560 (e.g., by a tool that engages the socket 166) causes axial movement of the plug 560 in the direction of arrow A (FIG. 18A).

Referring to FIG. 18B, responsive to rotation of the plug 560, the plug 60 moves to a second axial position relative to the body 510, and the plurality of deflectable portions 522A-522D move from the first generally inward position (FIG. 18A). As shown by a comparison between FIG. 18A and FIG. 18B, the plug 560 moves in the direction of arrow A responsive to rotation (e.g., by a tool) such that the tip portion 562 of the plug 560 directly engages the plurality of deflectable portions 522A-522D of the body 510, causing the each of the plurality of deflectable portions 522A-522D to move radially outward relative to the rest of the body 510 and a central axis of the glenoid implant 500. As shown in FIG. 18B, movement of the plug 560 in the direction of arrow A causes the plurality of deflectable portions 522A-522D to engage or contact the outer edges of the cavity in the bone B (e.g., spongey bone material).

Referring to FIG. 18C, responsive to continued rotation of the plug 560, the plug 560 moves to a third axial position relative to the body 510, and the plurality of deflectable portions 522A-522D move to a second generally outward position relative to the body 510. As shown by a comparison between FIG. 18B and FIG. 18C, continued movement of the plug 560 in the direction of arrow A causes the tip portion 562 to cause further radially outward movement of the plurality of deflectable portions 522A-522D. In the second generally outward position (FIG. 18C), the plurality of deflectable portions 522A-522D engage and protrude into the edges of the bone (e.g., spongey bone material) defining the cavity in the bone B. The engagement between the plurality of deflectable portions 522A-522D and the bone material aids in securing the glenoid implant 500 to the bone B and/or promotes osseointegration of the glenoid implant 500.

Because each of the plurality of deflectable portions 522A-522D have an inwardly tapered inner surface that engage the tip portion 562 of the plug 560 when the plug 560 moves in the direction of arrow A, each of the plurality of deflectable portions 522A-522D engage and protrude into the spongy bone material at an angle (e.g., between about 1 degree and about 25 degrees). That is, the plurality of deflectable portions 522A-522D move both horizontally into the bone material and vertically in the opposite direction of arrow A. As shown by a comparison between FIG. 18A and FIG. 18C, moving the plurality of deflectable portions 522A-522D to the second generally outward position pulls the plate 514 down in the direction of arrow A due to the angle at which the plurality of deflectable portions 522A-522D contact the spongy bone of the opening in the bone B, further aiding in securing the glenoid implant 500 to the bone B.

Each of the plurality of deflectable portions 522A-522D move by a predetermined distance between the first generally inward position (FIG. 18A) and the second generally outward position (FIG. 18C). The predetermined distance can be, for example, between about 0.5 millimeters and about 1.5 millimeters, between about 0.25 millimeters and about 2.5 millimeters, between about 0.1 millimeters and about 3 millimeters, etc. Preferably, the predetermined distance is between about 0.5 millimeters and about 1.5 millimeters. In this manner, the overall diameter of the body 510 of the glenoid implant 500 that is positioned in the opening in the bone B can increase by between about 1 millimeter and about 3 millimeters to aid in securing the glenoid implant 500 to the bone (e.g., scapula).

Figure 19:
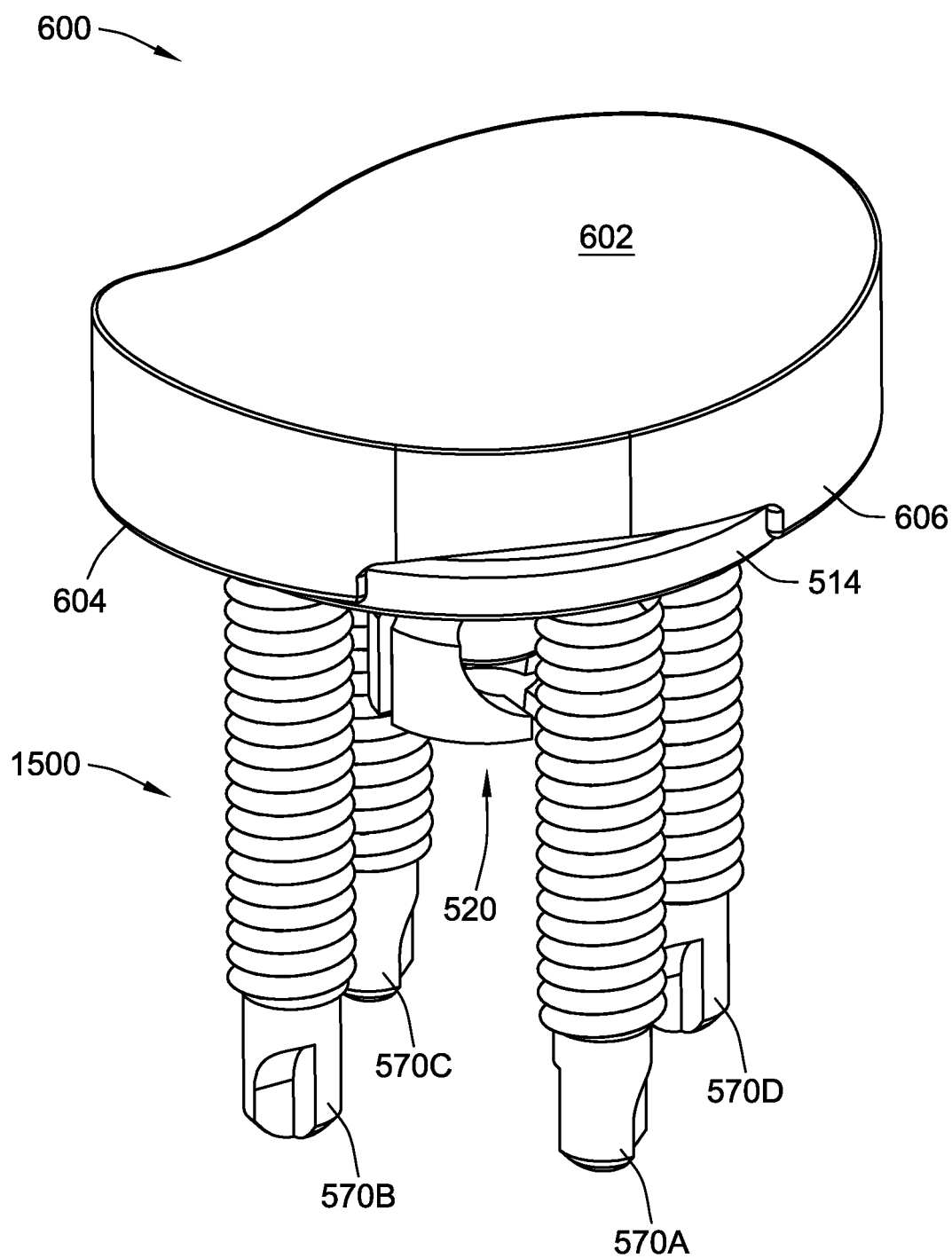
FIG. 19 is a perspective view of the glenoid implant of FIG. 16 coupled to a glenoid component, according to some implementations of the present disclosure.

Referring to FIG. 19, in some implementations, the glenoid implant 500 can be used for an anatomic shoulder replacement procedure. In such implementations, a glenoid component 600 is coupled to the glenoid implant 500. The glenoid component 600 is the same as, or similar to, the glenoid component 300 (FIGS. 12 and 13) described above and includes an outer surface 602 and a first rim portion 604 and a second rim portion 606 that engage a portion of the plate 514 of the glenoid implant 500 to form a press fit connection to secure the glenoid component 600 to the glenoid implant 500.

Figure 20:
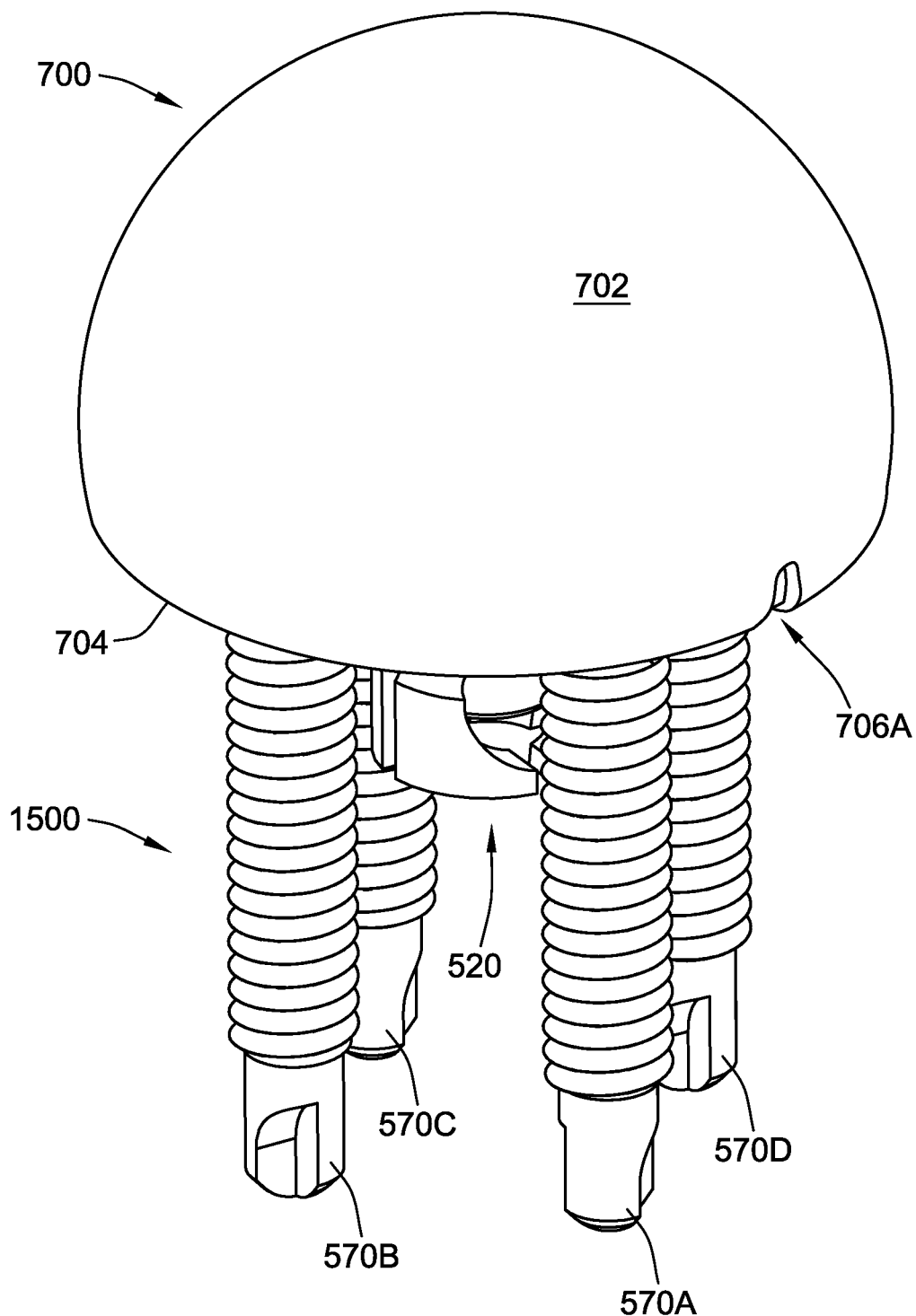
FIG. 20 is a perspective view of the glenoid implant of FIG. 16 coupled to a glenosphere, according to some implementations of the present disclosure.

Referring to FIG. 20, in some implementations, the glenoid implant 500 can be used for a reverse shoulder replacement procedure. In such implementations, a glenosphere 700 is coupled to the glenoid implant 500. The glenosphere 700 is the same as, or similar to, the glenosphere 400 (FIGS. 14 and 15) described above and includes an outer surface 702, an outer rim 704 that engages the plate 514 to form a press fit connection to aid in securing the glenosphere 700 to the glenoid implant 500, and a notch 706A that aids in permitting the glenosphere 700 to flex to form a press fit on the plate 514.

Figure 21:
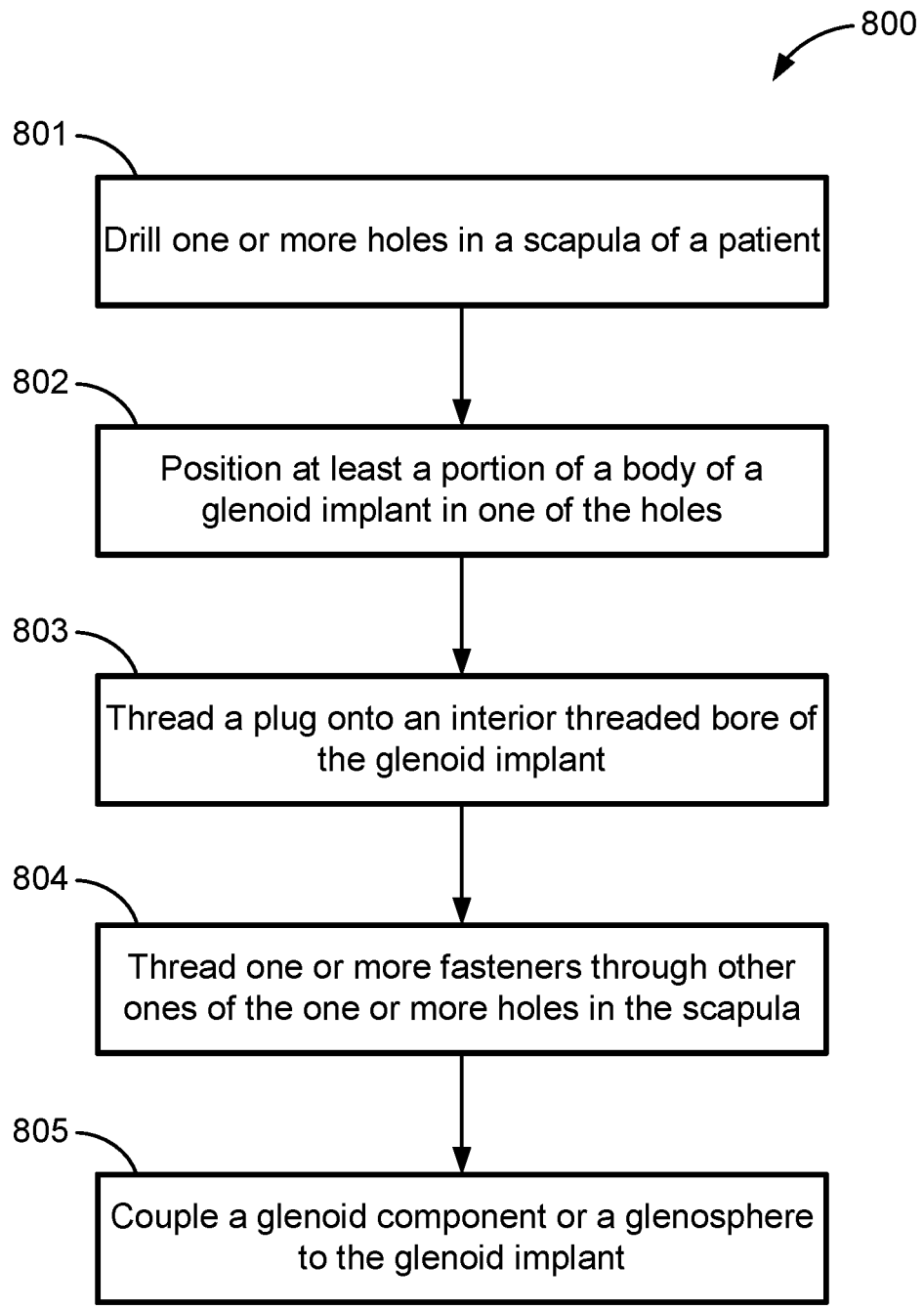
FIG. 21 is a process flow diagram for a method of installing a glenoid implant, according to some implementations of the present disclosure.

Referring to FIG. 21, a method 800 for installing a glenoid implant according to some implementations of the present disclosure is illustrated. The method 800 can be implemented using the glenoid implant 100 (FIGS. 1A-11B) or the glenoid implant 500 (FIGS. 16-18C) described herein for either an anatomical shoulder replacement procedure or a reverse shoulder replacement procedure.

Step 801 of the method 800 forming (e.g., drilling) one or more holes in a bone (e.g., scapula) of a patient. For example, step 801 can include forming (e.g. drilling) a first hole or cavity in the scapula that receives at least a portion of a body of a glenoid implant (step 802). Step 801 can also include forming or drilling a plurality of holes for receiving fasteners therein (step 804).

Step 802 of the method 800 includes positioning at least a portion of a glenoid implant in one of the holes or cavities in the bone of the patient. For example, step 802 can include positioning a portion of the body 110 of the glenoid implant 100 in the cavity in the scapula of the patient as shown in FIG. 9B. As another example, step 802 can include positioning a portion of the body 510 of the glenoid implant 500 in the cavity in the scapula of the patient as shown in FIG. 18A.

Step 803 of the method 800 includes threading a plug into an interior threaded bore of the glenoid implant. For example, step 803 can include threading the plug 160 of the glenoid implant 100 into the interior threaded bore 138 of the collet 130 to cause the plurality of fins 150A-150D to move from the first generally inward position (FIG. 9B) to the second generally outward position (FIG. 11B) to secure the glenoid implant 100 to the bone. As another example, step 803 can include threading the plug 560 of the glenoid implant 500 into the interior threaded bore 512 of the body 510 to cause the plurality of deflectable portions 522A-522D to move from the first generally inward position (FIG. 18A) to the second generally outward position (FIG. 18C) to secure the glenoid implant 500 to the bone. Step 803 can include using a tool to rotate the plug and cause the plug to threadingly engage the interior threaded bore.

Step 804 of the method 800 includes threading one or more fasteners through other ones of the one or more holes in the bone (step 801). Step 804 can include using a tool to rotate the one or more fasteners. For example, step 804 can include positioning the plurality of fasteners 170A-170D (FIGS. 1A-1B) of the glenoid implant 100 through the plurality of apertures 115A-115D in the plate 514 (FIGS. 3A-3B) such that the plurality of fasteners 170A-170D threadingly engage a corresponding one of the holes formed or drilled in the bone. As another example, step 804 can include positioning the plurality of fasteners 570A-570D (FIG. 16) of the glenoid implant 500 through the plurality of apertures 515A-515D in the plate 514 (FIG. 17A) such that the plurality of fasteners 570A-570D threadingly engage a corresponding one of the holes formed or drilled in the bone.

In some implementations, step 804 is performed subsequent to step 803. In other implementations, step 804 is performed prior to step 803, but subsequent to step 802. In either implementation, steps 802-804 are performed prior to step 805.

Step 805 of the method 800 includes coupling a glenoid component or a glenosphere to the glenoid implant. For example, step 805 can include coupling the glenoid component 300 to the glenoid implant 100 (FIGS. 12 and 13) as described above for an anatomical shoulder replacement procedure, or coupling the glenosphere 400 to the glenoid implant 100 (FIGS. 14 and 15) as described above for a reverse shoulder replacement procedure. As another example, step 805 can include coupling the glenoid component 600 to the glenoid implant 500 (FIG. 19) as described above for an anatomical shoulder replacement procedure, or coupling the glenosphere 700 to the glenoid implant 500 as described above for a reverse shoulder replacement procedure.

One or more elements or aspects or steps, or any portion(s) thereof, from one or more of any of claims 1-70 below can be combined with one or more elements or aspects or steps, or any portion(s) thereof, from one or more of any of the other claims 1-70 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A glenoid implant comprising:
   a body having a central aperture therethrough and including a boss coupled to and extending from a plate, the boss including a plurality of slots;
   a plurality of fins, each of the plurality of fins being coupled with a respective one of the plurality of slots of the boss of the body such that each of the plurality of fins is configured to move from a first generally inward position towards a second generally outward position;
   a collet including an interior threaded bore and a plurality of deflectable arms, the collet being configured to be at least partially received within the central aperture of the body such that each of the plurality of deflectable arms is generally adjacent to a respective one of the plurality of slots of the boss of the body; and
   a plug including an exterior threaded portion and a tip portion, the exterior threaded portion of the plug being configured to threadingly engage with the interior threaded bore of the collet such that the tip portion of the plug is configured to engage with and cause the plurality of deflectable arms of the collet to move and cause the plurality of fins to move from the first generally inward position towards the second generally outward position, thereby aiding in securing the body to a scapula of a patient.

2. The glenoid implant of claim 1, further comprising one or more of a glenoid component coupled to the plate and a glenosphere coupled to the plate.

3. The glenoid implant of claim 1, wherein each of the plurality of deflectable arms has an inwardly tapered surface configured to engage the tip portion of the plug.

4. The glenoid implant of claim 1, wherein each of the plurality of fins includes an interior portion, a middle portion, and an exterior portion, the interior portion of each of the plurality of fins being positioned between the plurality of deflectable arms of the collet and an inner surface of the boss, the middle portion of each of the plurality of fins being at least partially disposed within a corresponding one of the plurality of slots of the boss, and wherein the interior portion of the plurality of fins has one or more of a curved shape and a tapered surface, and wherein the exterior portion of each of the plurality of fins has one or more of a curved shape and a wedge shape.

5. The glenoid implant of claim 1, wherein the plate includes a plurality of apertures extending from the upper surface of the plate through the opposing lower surface, the plurality of apertures being concentrically arranged about the central aperture, and further comprising a plurality of fasteners, each of the plurality of fasteners being configured to be received in a corresponding one of the plurality of apertures of the plate, and wherein each of the plurality of fasteners includes one or more locking screws and includes a threaded portion and an unthreaded portion having a flute.

6. The glenoid implant of claim 1, wherein the plate and the boss are generally cylindrical, and wherein the plate has a first diameter and the boss has a second diameter that is less than the first diameter of the plate.

7. The glenoid implant of claim 1, wherein each of the plurality of slots is positioned circumferentially about the boss, and wherein each of the plurality of slots extends in an axial direction.

* * * * *